US009909187B2

(12) United States Patent
Ho et al.

(10) Patent No.: US 9,909,187 B2
(45) Date of Patent: Mar. 6, 2018

(54) DETECTION OF SINGLE NUCLEOTIDE POLYMORPHISMS IN HUMAN KRAS

(71) Applicant: Abbott Molecular Inc., Des Plaines, IL (US)

(72) Inventors: Shiaolan Y. Ho, Wilmette, IL (US); Ankur H. Shah, Carpentersville, IL (US); Xiaodi Chen, Des Plaines, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 124 days.

(21) Appl. No.: 14/748,155

(22) Filed: Jun. 23, 2015

(65) Prior Publication Data

US 2015/0368725 A1    Dec. 24, 2015

Related U.S. Application Data

(60) Provisional application No. 62/016,312, filed on Jun. 24, 2014.

(51) Int. Cl.
| | | |
|---|---|---|
| *C12Q 1/68* | (2006.01) | |
| *C12P 19/34* | (2006.01) | |
| *C07H 21/02* | (2006.01) | |
| *C07H 21/04* | (2006.01) | |

(52) U.S. Cl.
CPC ..... *C12Q 1/6886* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,800,195 A | 1/1989 | Burgess et al. |
| 4,965,188 A | 10/1990 | Mullis et al. |
| 5,310,652 A | 5/1994 | Gelfand et al. |
| 5,310,893 A | 5/1994 | Erlich et al. |
| 5,322,770 A | 6/1994 | Gelfand |
| 5,451,512 A | 9/1995 | Apple et al. |
| 5,468,613 A | 11/1995 | Erlich et al. |
| 5,484,908 A | 1/1996 | Froehler et al. |
| 5,502,177 A | 3/1996 | Matteucci et al. |
| 5,539,082 A | 7/1996 | Nielsen et al. |
| 5,561,058 A | 10/1996 | Gelfand et al. |
| 5,604,099 A | 2/1997 | Erlich et al. |
| 5,641,864 A | 6/1997 | Gelfand |
| 5,645,985 A | 7/1997 | Froehler et al. |
| 5,693,517 A | 12/1997 | Gelfand et al. |
| 5,763,588 A | 6/1998 | Matteucci et al. |
| 5,783,699 A | 7/1998 | Mattingly et al. |
| 5,830,653 A | 11/1998 | Froehler et al. |
| 6,005,096 A | 12/1999 | Matteucci et al. |
| 6,007,992 A | 12/1999 | Lin et al. |
| 6,028,183 A | 2/2000 | Lin et al. |
| 2004/0014105 A1 | 1/2004 | Schroeder et al. |
| 2005/0227257 A1 | 10/2005 | Abravaya et al. |
| 2011/0129832 A1* | 6/2011 | Makarov ............... C12Q 1/6818 435/6.11 |
| 2013/0224740 A1* | 8/2013 | Thierry ................ C12Q 1/6886 435/6.11 |

FOREIGN PATENT DOCUMENTS

| | | |
|---|---|---|
| CN | 102304581 | 1/2012 |
| CN | 103114146 | 5/2013 |
| EP | 1319710 | 6/2003 |
| WO | 9220702 A1 | 11/1992 |
| WO | 9220703 A1 | 11/1992 |

OTHER PUBLICATIONS

Lang et al. J. Mol. Diagnosis. Jan 2011. 13(1): 23-28.*
Voutsina et al (Modern Pathology. Aug. 31, 2012. 26: 302-313.*
Mitsuhashi et al (Journal of Laboratory Analysis. 1996. 10: 285-293.*
NCBI Database. GenBank Accession No. NG_007524, Mar. 24, 2013 (National Center for Biotechnology Information, National Library of Medicine, Bethesda, MD, USA).*
Diderot et al Experimental and Molecular Pathology. Mar. 7, 2012. 92: 275-280.*
International Search Report for Application No. PCT/US2015/037268 dated Sep. 14, 2015.
Written Opinion for Application No. PCT/US2015/037268 dated Sep. 14, 2015.
Egholm M., et al., "PNA Hybridizes to Complementary Oligonucleotides Obeying the Watson-Crick Hydrogen-Bonding Rules," Nature, 1993, vol. 365 (6446), pp. 566-568.
Hancock D.K., et al., "Design and Use of a Peptide Nucleic Acid for Detection of the Heteroplasmic Low-Frequency Mitochondrial Encephalomyopathy, Lactic Acidosis, and Stroke-Like Episodes (MELAS) Mutation in Human Mitochondrial DNA," Clinical Chemistry, 2002, vol. 48 (12), pp. 2155-2163.
Hanvey J.C., et al., "Antisense and Antigene Properties of Peptide Nucleic Acids," Science, 1992, vol. 258 (5087), pp. 1481-1485.
Hyrup B., et al., "Peptide Nucleic Acids (PNA): Synthesis, Properties and Potential Applications," Bioorganic and Medicinal Chemistry, 1996, vol. 4 (1), pp. 5-23.
Karadag A., et al., "A Novel Technique Based on a PNA Hybridization Probe and FRET Principle for Quantification of Mutant Genotype in Fibrous Dysplasia/Mccune-Albright Syndrome," Nucleic Acids Research, 2004, vol. 32 (7), p. e63.

(Continued)

*Primary Examiner* — Carla J Myers
(74) *Attorney, Agent, or Firm* — Lisa V. Mueller; Michael Best & Friedrich LLP

(57) ABSTRACT

Disclosed herein are primers and probes for the detection of single nucleotide polymorphisms (SNPs) in the KRAS gene. These primers and probes may be used in a method of identifying the presence or absence of one or more SNPs in the KRAS gene. These primers and probes may also be used in a method of predicting a response of a subject in need thereof to a cancer therapy. The primers and probes may further be used in a method of selecting a cancer therapy for a subject in need thereof.

2 Claims, 3 Drawing Sheets

(56) References Cited

OTHER PUBLICATIONS

Kirishima T., et al., "Detection of YMDD Mutant Using a Novel Sensitive Method in Chronic Liver Disease Type B Patients Before and During Lamivudine Treatment," Journal of Hepatology, 2002, vol. 37 (2), pp. 259-265.

Kobayashi M., et al., "Fluorescence-Based DNA Minisequence Analysis for Detection of Known Single-Base Changes in Genomic DNA," Molecular and Cellular Probes, 1995, vol. 9 (3), pp. 175-182.

Kyger E.M., et al., " Detection of the Hereditary Hemochromatosis Gene Mutation by Real-Time Fluorescence Polymerase Chain Reaction and Peptide Nucleic Acid Clamping," Analytical Biochemistry, 1998, vol. 260 (2), pp. 142-148.

Nielsen P.E., et al., "Sequence-selective Recognition of DNA by Strand Displacement with a Thymine-substituted Polyamide," Science, 1991, vol. 254 (5037), pp. 1497-1500.

Ohishi W., et al., "Identification of Rare Polymerase Variants of Hepatitis B Virus Using a Two-Stage PCR with Peptide Nucleic Acid Clamping," Journal of Medical Virology, 2004, vol. 72 (4), pp. 558-565.

Orum H., et al., "Single Base Pair Mutation Analysis by PNA Directed PCR Clamping," Nucleic Acids Research, 1993, vol. 21 (23), pp. 5332-5336.

Sun X., et al., "Detection of Tumor Mutations in the Presence of Excess Amounts of Normal DNA," Nature Biotechnology, 2002, vol. 20 (2), pp. 186-189.

Taback B., et al., "Peptide Nucleic Acid Clamp PCR: A Novel K-Ras D Mutation Detection Assay for Colorectal Cancer Micrometastases in Lymph Nodes," 2004, vol. 111 (3), pp. 409-414.

Takiya T., et al., "Identification of Single Base-pair Mutation on uidA Gene of *Escherichia coli* 0157:H7 by Peptide Nucleic Acids (PNA) Mediated PCR Clamping," Bioscience, Biotechnology and Biochemistry, 2004, vol. 68 (2), pp. 360-368.

Thiede C., et al., "Simple and Sensitive Detection of Mutations in the Ras Proto-Oncogenes Using PNA-Mediated PCR Clamping," 1996, vol. 24 (5), pp. 983-984.

Amicarelli, G. et al., "FLAG assay as a novel method for real-time signal generation during PCR: application to detection and genotyping of KRAS codon 12 mutations," Nucl. Acids Res. (2007) 35(19):e131-138.

Ugorcakova, J. et al., "Detection of point mutations in KRAS oncogene by real-time PCR-based genotyping assay in GIT diseases," Bratisl Lek Listy (2012) 113(2):73-79.

\* cited by examiner

| Fluorescent Channels | Reaction 1 | Reaction 2 | Reaction 3 |
|---|---|---|---|
| FAM | G12C | G12D | G13D |
| VIC | G12R | G12A | G13C |
| Cy5 | G12S | G12V | Q61H |

FIG. 3

DETECTION OF SINGLE NUCLEOTIDE POLYMORPHISMS IN HUMAN KRAS

TECHNICAL FIELD

The present invention relates to single nucleotide polymorphisms (SNPs) in human KRAS, to methods of identifying the presence or absence of one or more SNPs in human KRAS, to methods of selecting a cancer therapy, and to methods of predicting a response to a cancer therapy.

BACKGROUND

The gene v-Ki-ras2 Kirsten rat sarcoma viral oncogene homolog (KRAS) is associated with a wide variety of cancers, for example, colorectal cancer and non-small cell lung cancer. In particular, cancer may be associated with mutations in codons 12, 13, and 61 of the KRAS gene, namely single nucleotide polymorphisms (SNPs). These SNPs may be indicative of the responsiveness of a subject suffering from cancer to one or more cancer therapies or treatments. In turn, this prediction aides in the selection of the cancer therapy to administer to the subject.

Present assays for detecting these SNPs include amplification-based assays that are capable of detecting multiple SNPs in two reaction mixtures. Such assays, however, do not identify the specific mutation present, but rather only detect if any mutation is or is not present. By failing to identify the identity of the SNPs present or absent, these assays do not allow a user to predict the response of the subject suffering from cancer to one or more cancer therapies, thereby hindering the selection of a cancer therapy for the subject. Other amplification-based assays identify the specific SNP, but to do so, require one reaction mixture per SNP, and thus, require a larger sample input. Samples for diagnostic testing are typically small in size, and therefore, use of a larger amount of sample in one assay limits the ability to test for additional markers in another assay.

Accordingly, a need exists for the development of methods that detect and identify multiple SNPs in the KRAS gene with a minimal amount of sample input to facilitate the prediction of a subject's response to one or more cancer therapies. The identification of particular SNPs for the KRAS gene will further allow practitioners to select the appropriate cancer therapy for the subject.

SUMMARY OF THE INVENTION

The present invention is directed to a primer comprising a nucleotide sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:43, SEQ ID NO:44, SEQ ID NO:45, SEQ ID NO:46, SEQ ID NO:47, and SEQ ID NO:48.

The present invention is also directed to a primer set comprising (a) a forward primer selected from the group consisting of: SEQ ID NO:2, SEQ ID NO:7, and SEQ ID NO:43; (b) a reverse primer selected from the group consisting of: SEQ ID NO:6, SEQ ID NO:11, and SEQ ID NO:48; and (c) a peptide nucleic acid oligomer selected from the group consisting of SEQ ID NO:52 and SEQ ID NO:56. The primer set may be selected from the group consisting of: (a) SEQ ID NO:2, SEQ ID NO:6, and SEQ ID NO:52; (b) SEQ ID NO:2, SEQ ID NO:6, SEQ ID NO:43, SEQ ID NO:48, and SEQ ID NO:52; (c) SEQ ID NO:2, SEQ ID NO:6, SEQ ID NO:7, SEQ ID NO:11, SEQ ID NO:52, and SEQ ID NO:56; (d) SEQ ID NO:2, SEQ ID NO:6, SEQ ID NO:7, SEQ ID NO:11, SEQ ID NO:43, SEQ ID NO:48, SEQ ID NO:52, and SEQ ID NO:56; (e) SEQ ID NO:7, SEQ ID NO:11, and SEQ ID NO:56; and (f) SEQ ID NO:7, SEQ ID NO:11, SEQ ID NO:43, SEQ ID NO:48, and SEQ ID NO:56.

The present invention is also directed to a probe comprising a nucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:49, SEQ ID NO:50, and SEQ ID NO:51. The probe may comprise a nucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:49, SEQ ID NO:50, and SEQ ID NO:51 combined with a detectable label. The detectable label may be a fluorescent label. The fluorescent label may be selected from the group consisting of: FAM, NED, Cy5, and VIC. The probe may further comprise a quencher moiety.

The present invention is also directed to a probe may further comprise a nucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:49, SEQ ID NO:50, and SEQ ID NO:51 combined with a detectable label wherein the detectable label may be a fluorescent label. The fluorescent label may be selected from the group consisting of: FAM, NED, Cy5, and VIC.

The present invention is also directed to a probe comprising a nucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:49, SEQ ID NO:50, and SEQ ID NO:51. The probe may further comprise a nucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:49, SEQ ID NO:50, and SEQ ID NO:51 combined with a detectable label and a quencher moiety. The detectable label may be a fluorescent label. The fluorescent label may be selected from the group consisting of: FAM, NED, Cy5, and VIC.

The present invention is also directed to a primer and probe set comprising (a) one or more forward primers selected from the group consisting of: SEQ ID NO:1, SEQ ID NO:2, SEQ ID NO:3, SEQ ID NO:7, SEQ ID NO:8, and SEQ ID NO:9; (b) one or more reverse primers selected from the group consisting of: SEQ ID NO:4, SEQ ID NO:5, SEQ ID NO:6, SEQ ID NO:10, SEQ ID NO:11, and SEQ ID NO:12; (c) one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and (d) one or more peptide nucleic oligomers selected from the group consisting of SEQ ID NO:52, SEQ ID NO:53, SEQ ID NO:54, SEQ ID NO:55, SEQ ID NO:56, and SEQ ID NO:57.

The one or more probes may be selected the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42 and further comprise a detectable label. The detectable label may be a fluorescent label. The fluorescent label may be selected from the group consisting of: FAM, NED, Cy5, and VIC. The one or more probes may be selected the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42 and further comprise a detectable label, and may further comprise a quencher moiety.

The primer and probe set may further comprise an internal control set comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50 or SEQ ID NO:51. The probe comprising the nucleotide sequence as set forth in SEQ ID NO:49, SEQ ID NO:50 or SEQ ID NO:51 may further comprise a detectable label. The detectable label may be a fluorescent label. The probe comprising the nucleotide sequence as set forth in SEQ ID NO:49, SEQ ID NO:50 or SEQ ID NO:51 may further comprise a quencher moiety.

The primer and probe set may be selected from the group consisting of: (a) SEQ ID NO:2, SEQ ID NO:6, SEQ ID NO:43, SEQ ID NO:48, SEQ ID NO:52, SEQ ID NO:22, SEQ ID NO:27, SEQ ID NO:30, and SEQ ID NO:51; (b) SEQ ID NO:2, SEQ ID NO:6, SEQ ID NO:43, SEQ ID NO:48, SEQ ID NO:52, SEQ ID NO:13, SEQ ID NO:16, SEQ ID NO:20, and SEQ ID NO:51; and (c) SEQ ID NO:2, SEQ ID NO:6, SEQ ID NO:7, SEQ ID NO:11, SEQ ID NO:43, SEQ ID NO:48, SEQ ID NO:52, SEQ ID NO:56, SEQ ID NO:31, SEQ ID NO:34, SEQ ID NO:38, SEQ ID NO:40, and SEQ ID NO:51.

The present invention is also directed to a primer and probe set comprising (a) one or more forward primers selected from the group consisting of: SEQ ID NO:1, SEQ ID NO:2, SEQ ID NO:3, SEQ ID NO:7, SEQ ID NO:8, and SEQ ID NO:9; (b) one or more reverse primers selected from the group consisting of: SEQ ID NO:4, SEQ ID NO:5, SEQ ID NO:6, SEQ ID NO:10, SEQ ID NO:11, and SEQ ID NO:12; (c) one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and (d) one or more peptide nucleic oligomers selected from the group consisting of SEQ ID NO:52, SEQ ID NO:53, SEQ ID NO:54, SEQ ID NO:55, SEQ ID NO:56, and SEQ ID NO:57. In the primer and probe set, the one or more probes may comprise a detectable label. This detectable label may be a fluorescent label, in which the fluorescent label is selected from the group consisting of: FAM, NED, Cy5, and VIC. In the primer and probe set, the one or more probes may further comprise a quencher moiety.

The present invention is also directed to a primer and probe set comprising (a) one or more forward primers selected from the group consisting of: SEQ ID NO:1, SEQ ID NO:2, SEQ ID NO:3, SEQ ID NO:7, SEQ ID NO:8, and SEQ ID NO:9; (b) one or more reverse primers selected from the group consisting of: SEQ ID NO:4, SEQ ID NO:5, SEQ ID NO:6, SEQ ID NO:10, SEQ ID NO:11, and SEQ ID NO:12; (c) one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and (d) one or more peptide nucleic oligomers selected from the group consisting of SEQ ID NO:52, SEQ ID NO:53, SEQ ID NO:54, SEQ ID NO:55, SEQ ID NO:56, and SEQ ID NO:57. This primer and probe set may further comprise an internal control set comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50 or SEQ ID NO:51. This primer and probe set may be selected from the group consisting of: (a) SEQ ID NO:2, SEQ ID NO:6, SEQ ID NO:43, SEQ ID NO:48, SEQ ID NO:52, SEQ ID NO:22, SEQ ID NO:27, SEQ ID NO:30, and SEQ ID NO:51; (b) SEQ ID NO:2, SEQ ID NO:6, SEQ ID NO:43, SEQ ID NO:48, SEQ ID NO:52, SEQ ID NO:13, SEQ ID NO:16, SEQ ID NO:20, and SEQ ID NO:51; and (c) SEQ ID NO:2, SEQ ID NO:6, SEQ ID NO:7, SEQ ID NO:11, SEQ ID NO:43, SEQ ID NO:48, SEQ ID NO:52, SEQ ID NO:56, SEQ ID NO:31, SEQ ID NO:34, SEQ ID NO:38, SEQ ID NO:40, and SEQ ID NO:51.

The present invention is also directed to a primer and probe set comprising (a) one or more forward primers selected from the group consisting of: SEQ ID NO:1, SEQ ID NO:2, SEQ ID NO:3, SEQ ID NO:7, SEQ ID NO:8, and SEQ ID NO:9; (b) one or more reverse primers selected from the group consisting of: SEQ ID NO:4, SEQ ID NO:5, SEQ ID NO:6, SEQ ID NO:10, SEQ ID NO:11, and SEQ ID NO:12; (c) one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and (d) one or more peptide nucleic oligomers selected from the group consisting of SEQ ID NO:52, SEQ ID NO:53, SEQ ID NO:54, SEQ ID NO:55, SEQ ID NO:56, and SEQ ID NO:57. This primer and probe set may further comprise an internal control set comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50 or SEQ ID NO:51. In this primer and probe set, the probe comprising the nucleotide sequence as set forth in SEQ ID NO:49, SEQ ID NO:50 or SEQ ID NO:51 may further comprise a detectable label. In this primer and probe set, the probe comprising the nucleotide sequence as set forth in SEQ ID NO:49, SEQ ID NO:50 or SEQ ID NO:51 may also further comprise a quencher moiety. In this primer and probe set, the one or more probes may further comprise a detectable label.

The present invention is also directed to a method of identifying the presence or absence of one or more single nucleotide polymorphisms (SNPs) in v-Ki-ras2 Kirsten rat sarcoma viral oncogene homolog (KRAS), the method comprising: (a) forming a reaction mixture comprising (i) a sample obtained from the subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; and (c) detecting the one or more amplicons.

The reaction mixture may further comprise an internal control comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50, or SEQ ID NO:51.

The method of identifying may further comprise determining a difference in cycle number (ΔCN). The ΔCN may be a difference between a cycle number associated with an amplicon containing the SNP and a cycle number associated with an amplicon generated from the internal control. If the ΔCN is less than a cutoff value, then the SNP may be present in KRAS.

The method of identifying may further comprise identifying the presence of one or more SNPs in KRAS based upon the detection described in step (c) above.

In this method, the one or more SNPs may be selected from the group consisting of: G12C, G12R, G12S, G12D, G12A, G12V, G13D, G13C, and Q61H.

In this method, the one or more probes of the primer and probe set may comprise a detectable label. The detectable label may be a fluorescent label. The detectable label may be selected from the group consisting of: FAM, Cy5, NED, and VIC. The one or more probes of the primer and probe set of claim may further comprise a quencher moiety.

In this method, detecting may include measuring a fluorescent signal generated by the detectable label.

In this method, the primer and probe set of claim may be a primer and probe set selected from the group consisting of: (a) SEQ ID NO:2, SEQ ID NO:6, SEQ ID NO:52, SEQ ID NO:22, SEQ ID NO:27, and SEQ ID NO:30; (b) SEQ ID NO:2, SEQ ID NO:6, SEQ ID NO:52, SEQ ID NO:13, SEQ ID NO:16, and SEQ ID NO:20; and (c) SEQ ID NO:2, SEQ ID NO:6, SEQ ID NO:7, SEQ ID NO:11, SEQ ID NO:52, SEQ ID NO:56, SEQ ID NO:31, SEQ ID NO:34, SEQ ID NO:38, and SEQ ID NO:40.

In this method, the sample may be obtained from a cancerous tissue of the subject. The cancerous tissue may be a tissue from a colorectal cancer or a non-small cell lung cancer. The sample may be nucleic acid extracted from a fixed-formalin paraffin-embedded sample. The nucleic acid may be genomic DNA.

In this method, the sample may be a blood sample, a serum sample, or a plasma sample. The sample may be circulating tumor DNA (ctDNA).

In this method, forming the reaction mixture may comprise forming three reaction mixtures, each reaction mixture comprising the sample obtained from the subject and the primer and probe set. A first reaction mixture may comprise the sample obtained from the subject, the forward primer SEQ ID NO:2, the reverse primer SEQ ID NO:6, the peptide nucleic acid oligomer SEQ ID NO:52; and the probes SEQ ID NO:22, SEQ ID NO:27, and SEQ ID NO:30. A second reaction mixture may comprise the sample obtained from the subject, the forward primer SEQ ID NO:2, the reverse primer SEQ ID NO:6, the peptide nucleic acid oligomer SEQ ID NO:52; and the probes SEQ ID NO:13, SEQ ID NO:16, and SEQ ID NO:20. A third reaction mixture may comprise the sample obtained from the subject, the forward primer SEQ ID NO:2, the reverse primer SEQ ID NO:6, the forward primer SEQ ID NO:7, the reverse primer SEQ ID NO:11, the peptide nucleic acid oligomer SEQ ID NO:52, the peptide nucleic acid oligomer SEQ ID NO:56, and the probes SEQ ID NO:31, SEQ ID NO:34, SEQ ID NO:38, and SEQ ID NO:40.

Each of the first, second, and third reaction mixtures may further comprise an internal control comprising (a) a forward primer comprising a nucleotide sequence as set forth in SEQ ID NO:43; (b) a reverse primer comprising a nucleotide sequence as set forth in SEQ ID NO:48; and (c) a probe comprising a nucleotide sequence as set forth in SEQ ID NO:51.

The present invention is also directed to a method of identifying the presence or absence of one or more single nucleotide polymorphisms (SNPs) in v-Ki-ras2 Kirsten rat sarcoma viral oncogene homolog (KRAS), the method comprising: (a) forming a reaction mixture comprising (i) a sample obtained from the subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; and (c) detecting the one or more amplicons. In this method of identifying, the reaction mixture may further comprise an internal control comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50, or SEQ ID NO:51. This method of identifying may further comprise determining a difference in cycle number ($\Delta CN$). The $\Delta CN$ may be a difference between a cycle number associated with an amplicon containing the SNP and a cycle number associated with an amplicon generated from the internal control. If the $\Delta CN$ is less than a cutoff value, then the SNP may be present in KRAS.

The present invention is also directed to a method of identifying the presence or absence of one or more single nucleotide polymorphisms (SNPs) in v-Ki-ras2 Kirsten rat sarcoma viral oncogene homolog (KRAS), the method comprising: (a) forming a reaction mixture comprising (i) a sample obtained from the subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; and (c) detecting the one or more amplicons. This method of identifying may further comprise identifying the presence of one or more SNPs in KRAS based upon the detection in step (c). The one or more SNPs may be selected from the group consisting of: G12C, G12R, G12S, G12D, G12A, G12V, G13D, G13C, and Q61H.

The present invention is also directed to a method of identifying the presence or absence of one or more single nucleotide polymorphisms (SNPs) in v-Ki-ras2 Kirsten rat sarcoma viral oncogene homolog (KRAS), the method comprising: (a) forming a reaction mixture comprising (i) a sample obtained from the subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; and (c) detecting the one or more amplicons. In this method of identifying, the one or more probes of the primer and probe set may comprise a detectable label. The detectable label is a fluorescent label. In this method of identifying, the one or more probes of the primer and probe set may further comprise a quencher moiety. In this method of identifying, detecting may include measuring a fluorescent signal generated by the detectable label.

The present invention is also directed to a method of identifying the presence or absence of one or more single nucleotide polymorphisms (SNPs) in v-Ki-ras2 Kirsten rat sarcoma viral oncogene homolog (KRAS), the method comprising: (a) forming a reaction mixture comprising (i) a sample obtained from the subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; and (c) detecting the one or more amplicons. In this method of identifying, forming the reaction mixture may comprise forming three reaction mixtures, each reaction mixture comprising the sample obtained from the subject and the primer and probe set. In this method of identifying, a first reaction mixture may comprise the sample obtained from the subject, the forward primer SEQ ID NO:2, the reverse primer SEQ ID NO:6, the peptide nucleic acid oligomer SEQ ID NO:52; and the probes SEQ ID NO:22, SEQ ID NO:27, and SEQ ID NO:30. In this method of identifying, a second reaction mixture may comprise the sample obtained from the subject, the forward primer SEQ ID NO:2, the reverse primer SEQ ID NO:6, the peptide nucleic acid oligomer SEQ ID NO:52; and the probes SEQ ID NO:13, SEQ ID NO:16, and SEQ ID NO:20. In this method of identifying, a third reaction mixture may comprise the sample obtained from the subject, the forward primer SEQ ID NO:2, the reverse primer SEQ ID NO:6, the forward primer SEQ ID NO:7, the reverse primer SEQ ID NO:11, the peptide nucleic acid oligomer SEQ ID NO:52, the peptide nucleic acid oligomer SEQ ID NO:56, and the probes SEQ ID NO:31, SEQ ID NO:34, SEQ ID NO:38, and SEQ ID NO:40. Each of the first, second, and third reaction mixtures may further comprise an internal control comprising (a) a forward primer comprising a nucleotide sequence as set forth in SEQ ID NO:43; (b) a reverse primer comprising a nucleotide sequence as set forth in SEQ ID NO:48; and (c) a probe comprising a nucleotide sequence as set forth in SEQ ID NO:51.

The present invention is also directed to a method for selecting a cancer therapy for a subject in need thereof, the method comprising (a) forming a reaction mixture comprising (i) a sample obtained from a subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; (c) detecting the one or more amplicons; (d) identifying one or more single nucleotide polymorphisms (SNPs) in v-Ki-ras2 Kirsten rat sarcoma viral oncogene homolog (KRAS); and (e) selecting the cancer therapy for the subject based upon the one or more SNPs identified in step (d).

In this method for selecting the cancer therapy, the sample may be obtained from a cancerous tissue of the subject. The cancerous tissue may be a tissue from a colorectal cancer or a non-small cell lung cancer. The sample may be nucleic acid extracted from a fixed-formalin paraffin-embedded sample. The nucleic acid may be genomic DNA.

In this method for selecting the cancer therapy, the sample may be a blood sample, a serum sample, or a plasma sample. The sample may be circulating tumor DNA (ctDNA).

In this method for selecting the cancer therapy, the reaction mixture may further comprise an internal control comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50, or SEQ ID NO:51.

In this method for selecting the cancer therapy, identifying may include determining a difference in cycle number ($\Delta CN$). The $\Delta CN$ may be a difference between a cycle number associated with an amplicon containing the SNP and a cycle number associated with an amplicon generated from the internal control. If the $\Delta CN$ is less than a cutoff value, then the SNP may be present in KRAS. The one or more SNPs may be selected from the group consisting of: G12C, G12R, G12S, G12D, G12A, G12V, G13D, G13C, Q61H, and any combination thereof.

In this method for selecting the cancer therapy, the one or more probes of the primer and probe set may comprise a detectable label. The detectable label may be a fluorescent label. The fluorescent label may be selected from the group consisting of: FAM, Cy5, NED, and VIC. The one or more probes of the primer and probe set may further comprise a quencher moiety. In this method for selecting the cancer therapy, detecting may include measuring a fluorescent signal generated by the detectable label.

In this method for selecting the cancer therapy, selecting may include administering to the subject a therapy targeting epidermal growth factor receptor (EGFR) when the one or more SNPs are identified as being absent from KRAS. Selecting may include not administering to the subject a therapy targeting epidermal growth factor receptor (EGFR) when the one or more SNPs are identified as being present in KRAS. Selecting may include administering to the subject a therapy other than a therapy targeting epidermal growth factor receptor (EGFR) when the one or more SNPs are identified as being present in KRAS.

The present invention is also directed to a method for selecting a cancer therapy for a subject in need thereof, the method comprising (a) forming a reaction mixture comprising (i) a sample obtained from a subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; (c) detecting the one or more amplicons; (d) identifying one or more single nucleotide polymorphisms (SNPs) in v-Ki-ras2 Kirsten rat sarcoma viral oncogene homolog (KRAS); and (e) selecting the cancer therapy for the subject based upon the one or more SNPs identified in step (d). In this method for selecting the cancer therapy, the reaction mixture may further comprise an internal control comprising (a) a forward primer comprising a nucleotide sequence as set forth in SEQ ID NO:43, SEQ ID NO:44, or SEQ ID NO:45; (b) a reverse primer comprising a nucleotide sequence as set forth in SEQ ID NO:46, SEQ ID NO:47, or SEQ ID NO:48; and (c) a probe comprising a nucleotide sequence as set forth in SEQ ID NO:49, SEQ ID NO:50, or SEQ ID NO:51. In this method for selecting the cancer therapy, identifying may include determining a difference in cycle number ($\Delta$CN). The $\Delta$CN may be a difference between a cycle number associated with an amplicon containing the SNP and a cycle number associated with an amplicon generated from the internal control. If the $\Delta$CN is less than a cutoff value, then the SNP may be present in KRAS. The one or more SNPs may be selected from the group consisting of: G12C, G12R, G12S, G12D, G12A, G12V, G13D, G13C, Q61H, and any combination thereof. In this method for selecting the cancer therapy, the sample may be obtained from a cancerous tissue of the subject. The cancerous tissue may be a tissue from a colorectal cancer or a non-small cell lung cancer. The sample may be nucleic acid extracted from a fixed-formalin paraffin-embedded sample. The nucleic acid may be genomic DNA. In this method for selecting the cancer therapy, the sample may be a blood sample, a serum sample, or a plasma sample. The sample may be circulating tumor DNA (ctDNA).

The present invention is also directed to a method for selecting a cancer therapy for a subject in need thereof, the method comprising (a) forming a reaction mixture comprising (i) a sample obtained from a subject, wherein the sample is suspected of containing a KRAS target sequence and (ii) a primer and probe set comprising a. one or more forward primers selected from the group consisting of: SEQ ID NO:1, SEQ ID NO:2, SEQ ID NO:3, SEQ ID NO:7, SEQ ID NO:8, and SEQ ID NO:9; b. one or more reverse primers selected from the group consisting of: SEQ ID NO:4, SEQ ID NO:5, SEQ ID NO:6, SEQ ID NO:10, SEQ ID NO:11, and SEQ ID NO:12; c. one or more probes selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42; and d. one or more peptide nucleic oligomers selected from the group consisting of SEQ ID NO:52, SEQ ID NO:53, SEQ ID NO:54, SEQ ID NO:55, SEQ ID NO:56, and SEQ ID NO:57; (b) subjecting the reaction mixture to conditions sufficient for formation of one or more amplicons; (c) detecting the one or more amplicons; (d) identifying one or more single nucleotide polymorphisms (SNPs) in v-Ki-ras2 Kirsten rat sarcoma viral oncogene homolog (KRAS); and (e) selecting the cancer therapy for the subject based upon the one or more SNPs identified in step (d). In this method for selecting the cancer therapy, the one or more probes of the primer and probe set of may comprise a detectable label. The detectable label may be a fluorescent label. The one or more probes of the primer and probe set may further comprise a quencher moiety. In this method for selecting the cancer therapy, detecting may include measuring a fluorescent signal generated by the detectable label. Selecting may include administering to the subject a therapy targeting epidermal growth factor receptor (EGFR) when the one or more SNPs are identified as being absent from KRAS; not administering to the subject a therapy targeting epidermal growth factor receptor (EGFR) when the one or more SNPs are identified as being present in KRAS; or administering to the subject a therapy other than a therapy targeting epidermal growth factor receptor (EGFR) when the one or more SNPs are identified as being present in KRAS. The one or more SNPs may be selected from the group consisting of: G12C, G12R, G12S, G12D, G12A, G12V, G13D, G13C, Q61H, and any combination thereof.

BRIEF DESCRIPTION OF THE DRAWINGS

FIG. 3 shows a table listing the fluorescent channels used for the detection of the labeled probes, each of which detects one of the SNPs of FIG. 2. The internal control probe is also labeled and thus, detectable. Accordingly, four fluorescent channels are used for each reaction mixture because in each reaction mixture, each probe contains a different label with the exception that the probes for detecting Q61Ha and Q61Hb contain the same label as these mutations give rise to the same amino acid substitution, namely Q61H. Specifically, the four channels are detecting fluorescence from the labels NED, FAM, VIC, and Cy5.

DETAILED DESCRIPTION

Figure 1:
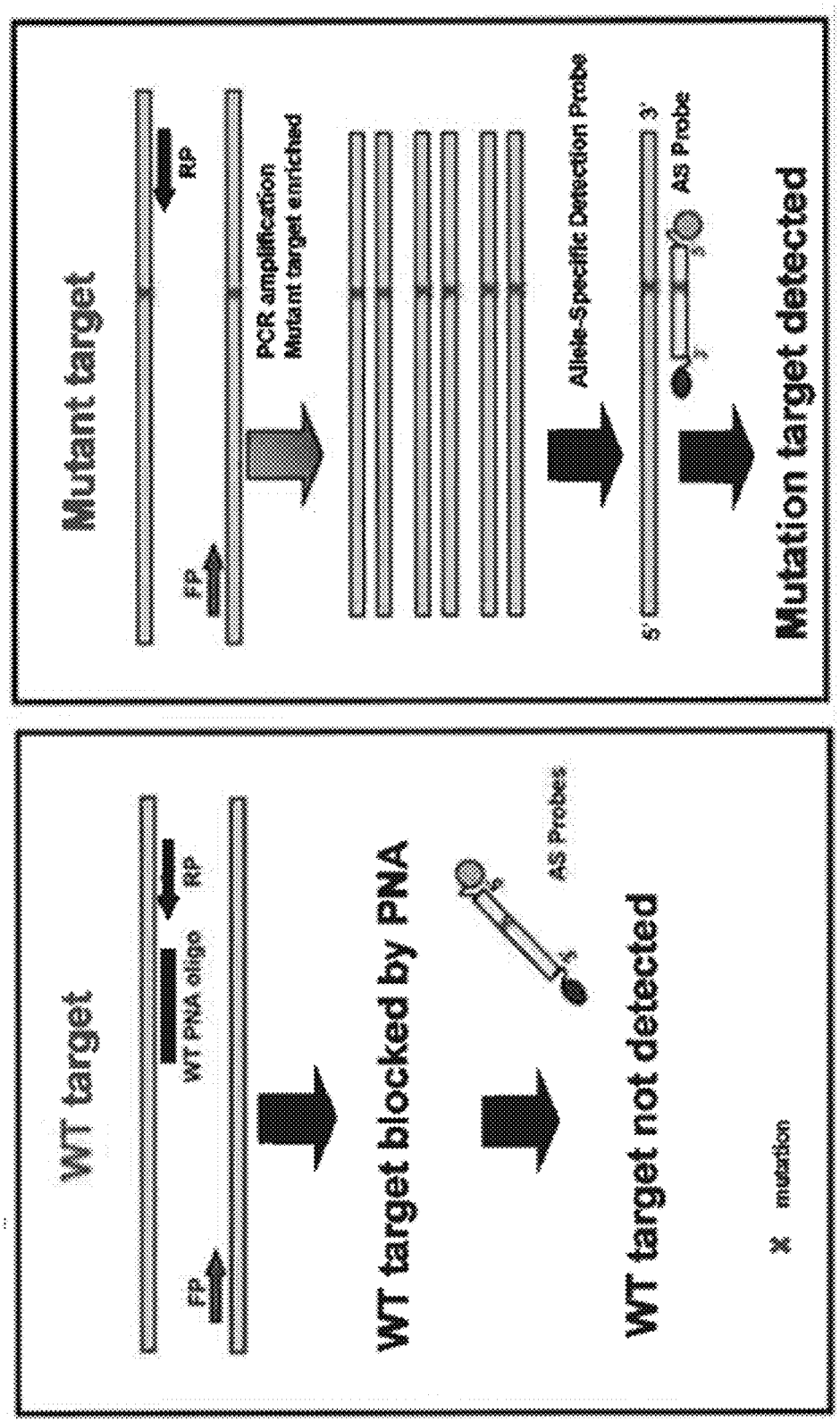
FIG. 1 shows a schematic illustrating the selective amplification and detection of a mutant KRAS sequence.

The present invention relates to primers and probes for identifying the presence or absence of one or more SNPs in KRAS in a subject in need thereof. The one or more SNPs may be present in codons 12, 13, and/or 61 of the KRAS gene.

The one or more SNPs in KRAS may be associated with a cancer, for example, but not limited to, a colorectal cancer (CRC) and a non-small cell lung cancer (NSCLC). The presence or absence of the one or more SNPs in KRAS may be indicative of a response of a subject suffering from a cancer (e.g., CRC or NSCLC) to a particular cancer therapy or treatment, and thus, aide in the selection of a cancer therapy for the subject.

The present invention also relates to a method of identifying the presence or absence of the one or more SNPs in KRAS. This method includes obtaining a sample from the subject, in which the sample is suspected of containing a KRAS target sequence. The KRAS target sequence may be a wild-type KRAS sequence, a mutant KRAS sequence, or a combination thereof. The method of identifying provides for the selective amplification and thus, enrichment of the mutant KRAS sequence. This selective amplification provides the advantageous properties of requiring less sample for the detection of the one or more SNPs in KRAS, and less interference or noise due to the amplification of the wild-type KRAS sequence.

The method of identifying also provides for the simultaneous amplification, detection and identification of multiple SNPs (such as up to 10, 9, 8, 7, 6, 5, 4, 3, 2, or 1 SNPs). This, in turn, provides the advantageous capability of determining the presence or absence of about 98%, about 97%, about 96%, about 95%, about 94%, about 93%, about 92%, about 91%, or about 90% of the mutations in KRAS that are associated with CRC and NSCLC with a small amount of sample input given the enrichment provided by the selective amplification of mutant KRAS sequences. In some embodiments, the method provides a sensitivity of at least about 2% KRAS mutation in 100 ng or 10 ng or ing or 1 μg or 10 μg or 100 μg of KRAS target sequence. The method also provides 100% reproducibility in the detection of the presence or absence of the one or more SNPs. The method further does not cross-react with nor is interfered by contaminating and/or interfering substances such as microorgansims, hemoglobin, triglycerides, necrotic tissue, homologous sequences, and so forth, which may be present in the sample obtained from the subject.

Accordingly, the method of identifying achieves the remarkable technical effect of detecting nearly all of the mutations in KRAS associated with CRC and NSCLC in a single assay. The method of identifying also achieves the remarkable technical effect of identifying which mutations are absent and which mutations are present in the KRAS gene of a given subject. Knowing which mutations are present or absent in the KRAS gene allows a user of the method to predict the response of a subject suffering from CRC or NSCLC to a given treatment. This prediction, in turn, allows the user to select and administer an appropriate treatment as described below in more detail.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "about" as used herein refers to approximately a ±10% variation from the stated value. It is to be understood that such a variation is always included in any given value provided herein, whether or not specific reference is made to it.

The term "fluorophore" or "fluorescent label" as used herein means any suitable moiety capable of emitting light. The light can be generated chemically, biologically, in response to excitational photons, or from any other suitable cause. Preferably, fluorophores are fluorescent organic dyes derivatized for attachment to the nucleic acids of the probes described herein via a linking moiety. When ribosyl or deoxyribosyl polymers are used to link the nucleobases together, the dyes can advantageously be derivatized to link to the terminal 3' carbon or terminal 5' carbon of the polymer.

The term "high-affinity nucleic acid analogue" as used herein means a modified nucleic acid that hybridizes to a complementary nucleic acid, such as a deoxyribonucleic acid (DNA), with higher affinity than an unmodified nucleic acid having the same base sequence. High-affinity nucleic acids include, but are not limited to, locked nucleic acids (LNAs), peptide nucleic acids (PNAs), hexitol nucleic acids (HNAs), phosphoramidates, and the like.

The term "hybridization" as used herein means the formation of a duplex structure by complementary base pairing between two single-stranded nucleic acids. Hybridization may occur between exactly complementary nucleic acid strands or between complementary nucleic acid strands that contain a low number of mismatches.

The term "KRAS target sequence" or "KRAS target nucleic acid sequence" as used herein means a nucleic acid encompassing codon 12, codon 13, codon 61, codon 117, or codon 146, or any combination thereof of a KRAS gene, or complements thereof, that is amplified, detected, or both using one or more of the primers and/or probes described herein. Additionally, while the term target sequence sometimes refers to a double-stranded nucleic acid sequence, a target sequence may also be single-stranded. In cases wherein the target sequence is double-stranded, primers of the present invention may amplify both strands of the target sequence. A target sequence may be selected that is more or less specific for a particular organism. For example, the target sequence may be specific to an entire genus, to more than one genus, to a species or subspecies, serogroup, auxotrope, serotype, strain, isolate, or other subset of organisms.

The term "label" as used herein means any moiety that can generate a detectable signal based upon the inherent chemical property of the moiety or its ability to react with another molecule. Examples of labels include, but are not limited to, radioactive, fluorescent, or chemiluminescent molecules or an enzyme. Labels also include molecules having affinity for other molecules that are readily detectable such as biotin-avidin systems and antigen-antibody systems.

The term "locked nucleic acid (LNA)" as used herein means a nucleic acid analogue (a polymer of purine and/or pyrimidine bases) characterized by the presence of one or more monomers that are conformationally restricted nucleotide analogues with an extra 2H—O, 4H—C-methylene bridge added to the ribose ring. LNA has been defined as an oligonucleotide having one or more 2H—O, 4H—C-methylene-(D-ribofuranosyl)nucleotide monomers. LNAs are resistant to exonucleases and heat.

The terms "nucleic acid," "nucleic acid sequence," "polynucleotide," and "oligonucleotide" mean a nucleic acid polymer of ribonucleic acid (RNA), deoxyribonucleic acid (DNA), modified RNA or DNA, or RNA or DNA mimetics (e.g., protein nucleic acids (PNAs)), and derivatives thereof, and variants thereof. Thus, polynucleotides include polymers composed of naturally occurring nucleobases, sugars, and covalent internucleoside (backbone) linkages as well as polymers having non-naturally occurring portions that function similarly. Oligonucleotides are generally short polynucleotides from about 10 to up to about 160 or 200 nucleotides.

These terms "nucleic acid," "nucleic acid sequence," "polynucleotide," and "oligonucleotide" also refer to primers, detectable oligonucleotides or probes, and oligomers, irrespective of length, and include polydeoxyribonucleotides, polyribonucleotides, and any other N-glycoside of a modified/unmodified, purine/pyrimidine base. Examples include single-stranded DNA (ssDNA), double-stranded DNA (dsDNA), single-stranded RNA (ssRNA), and double-stranded RNA (dsRNA). Such molecules can comprise phosphodiester linkages or modified linkages including, but not limited to, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations thereof. Such molecules can comprise adenine, guanine, thymine, cytosine and/or uracil, as well as other modified, non-standard, or derivatized bases. Alternatively or additionally, such molecules can comprise one or more modified sugar moieties.

The term "peptide nucleic acid (PNA)" as used herein means a synthetic DNA analog in which the normal phosphodiester backbone is replaced with a N-(2-aminoethyl) glycine chain or other alternative amino acid chain. Its nucleobases complement DNA or RNA in the same A-T(U) and G-C manner (Nielsen, et al., Science 254: 1497-1500 (1991); Hanvey, et al., Science 258: 1481-1485 (1992); and Egholm, et al., Nature 365: 566-568 (1993)). The artificial backbone renders PNA resistant to nucleases. PNA can be synthesized in accordance with methods known in the art (see, e.g., Hyrup, et al., Bioorg. Med. Chem. 4: 5-23 (1996); Int'l Pat. App. Pub. Nos. WO 92/20702 and 92/20703; and U.S. Pat. No. 5,539,082, the contents of all of which are incorporated herein by reference for their teachings regarding same). Two important features make PNA a superior PCR clamp for specific alleles. It cannot serve as a primer for polymerization. It cannot serve as a substrate for exonuclease activity by Taq polymerase. In addition, the melting temperature of a perfectly matched PNA-DNA duplex is higher than that of a DNA-DNA duplex of the same length; thus, the PNA-DNA duplex is more stable. A single mismatch in a PNA-DNA hybrid will cause a drop in the melting temperature of about 10-18° C. (Kyger, et al., Anal. Biochem. 260: 142-148 (1998)). Therefore, over an appropriate temperature range PNA can specifically block primer/detectable oligonucleotide annealing or chain elongation on a perfectly matched template without interfering with reactions on templates with mismatched base(s) (Sun, et al., Nat. Biotechnol. 20: 186-189 (2002); Thiede, et al., Nucleic Acids Res. 24: 983-984 (1996); and Taback, et al., Int. J. Cancer 111: 409-414 (2004)), which is referred to as PNA-mediated PCR clamping (Orum, et al., Nucleic Acids Res. 21: 5332-5336 (1993)). The large difference in melting temperature between perfectly matched and mismatched hybrids makes PNA a good sensor of point mutations (see, e.g., Karadag, et al., Nucleic Acids Res. 32: e63 (2004); Taback, et al. (2004), supra; Hancock, et al., Clin. Chem. 48: 2155-2163 (2002); Takiya, et al., Biosci. Biotechnol. Biochem. 68: 360-368 (2004); Kirishima, et al., J. Hepatol. 37: 259-265 (2002); and Ohishi, et al., J. Med. Virol. 72: 558-565 (2004)). U.S. Pat. App. Pub. No. 2004/0014105 discloses methods for the selective enrichment of polynucleotides that are present in a sample in low abundance. The method uses enzymatically non-extendable nucleobase oligomer (e.g., PNA) as a PCR clamp to block selectively polymerase activity on polynucleotides that are present in the sample in high abundance, thereby resulting in an enrichment of less abundant species in the sample. "PNA" may include a PNA clamp. Clamping operates by physical competition between a PNA and a DNA primer or probe for a common target site, thereby interfering with primer elongation.

The term "percent (%) nucleic acid sequence identity" as used herein with respect to nucleic acid sequences means the percentage of nucleotides in a candidate sequence that are identical with the nucleotides in the sequence of interest, after aligning the sequences and introducing gaps, if necessary, to achieve the maximum percent sequence identity. Alignment for the purposes of determining percent nucleic acid sequence identity may be achieved in various ways that are within the skill in the art, for example, using publicly available computer software such as BLAST, BLAST-2, ALIGN, or Megaalign (DNASTAR) software. Those skilled in the art can determine appropriate parameters for measuring alignment, including any algorithms needed to achieve maximal alignment over the full-length of the sequences being compared.

When nucleotide sequences are aligned, the percent nucleic acid sequence identity of a given nucleic acid sequence C to, with, or against a given nucleic acid sequence D (which may alternatively be phrased as a given nucleic acid sequence C that has or comprises a certain percent nucleic acid sequence identity to, with, or against a given nucleic acid sequence D) may be calculated as follows:

$$\text{percent nucleic acid sequence identity} = W/Z * 100$$

where

W is the number of nucleotides scored as identical matches by the sequence alignment program's or algorithm's alignment of C and D and Z is the total number of nucleotides in D.

When the length of nucleic acid sequence C is not equal to the length of nucleic acid sequence D, the percent nucleic acid sequence identity of C to D will not equal the percent nucleic acid sequence identity of D to C.

A first polynucleotide having sequence identity with a second polynucleotide means a first polynucleotide having at least about 60% nucleic acid sequence identity or at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% nucleic acid sequence identity with the second polynucleotide.

The term "polymerase chain reaction (PCR)" as used herein means a method of making copies of a DNA sequence. The method employs thermal cycling (i.e., cycles of heating and cooling for denaturation (or melting) and replication of the DNA, respectively). Primers, which are short DNA fragments containing sequences complementary to the DNA sequence to be copied, and a heat-stable DNA polymerase, such as the one from *Thermus aquaticus*, which is referred to as Taq polymerase, are used to select the DNA sequence and copy it (see, e.g., U.S. Pat. Nos. 4,683,195; 4,800,195, and 4,965,188, all of which are incorporated by reference herein for their teachings regarding same). With repeated cycling the copies, which are made, are used as templates for generating further copies (i.e., a chain reaction). PCR techniques include, but are not limited to, standard PCR, allele-specific PCR, assembly PCR, asymmetric PCR, digital PCR, Hot-start PCR, intersequence-specific PCR, inverse PCR, ligation-mediated PCR, methylation-specific PCR, mini-primer PCR, nested PCR, overlap-extension PCR, real-time PCR, reverse transcription-PCR, solid phase PCR, thermal asymmetric interlaced PCR, and Touchdown PCR.

The term "primer" as used herein means an oligonucleotide that initiates template-dependent nucleic acid synthesis. In the presence of a nucleic acid template, nucleoside triphosphate precursors, a polymerase, and cofactors, under suitable conditions of temperature and pH, the primer can be extended at its 3' terminus by the addition of nucleotides by the polymerase to yield a primer extension product. The primer may vary in length depending on the particular conditions employed and the purpose of the amplification. For example, a primer for amplification for a diagnostic purpose is typically from about 15 to about 35 nucleotides in length. The primer must be of sufficient complementarity to the desired template to prime the synthesis of the desired extension product. In other words, the primer must be able to anneal with the desired template strand in a manner sufficient to provide the 3' hydroxyl moiety of the primer in appropriate juxtaposition for use in the initiation of synthesis by a polymerase. It is not necessary for the primer to be an exact complement of the desired template. For example, a non-complementary nucleotide sequence can be present at the 5' end of an otherwise complementary primer. Alternatively, non-complementary bases can be interspersed within the oligonucleotide primer, provided that the primer sequence has sufficient complementarity with the sequence of the desired template strand to provide a template-primer complex for the synthesis of the extension product.

The term "probe" or "primer" as used herein means a polynucleotide that is at least 8 nucleotides, at least 10 nucleotides, at least 15 nucleotides, at least 20 nucleotides, or at least 25 nucleotides in length and forms a hybrid structure with a target sequence due to complementarity of at least one sequence in the probe or primer with a sequence in the target region. The polynucleotide regions of the probe may be composed of DNA and/or RNA and/or synthetic nucleotide analogs. Preferably, the probe does not contain a sequence that is complementary to the sequence or sequences used to prime for a target sequence during the polymerase chain reaction. The primer and the probe selectively hybridize to a target sequence under suitable conditions. The probe may be detected. In some embodiments, the primer and/or probe may contain one or more high-affinity nucleic acid analogues.

The term "specifically hybridize" as used herein means the ability of a nucleic acid (or an analog thereof) such as a primer or probe to bind specifically to another nucleic acid.

The term "subject" as used herein means a mammal, a bird, or a reptile. The subject may be a cow, horse, dog, cat, or a primate. The subject may be a human. The subject may be alive or dead.

The term "stringent" or "sequence-specific" hybridization conditions as used herein means conditions under which exactly complementary nucleic acid strands will preferentially hybridize. Stringent hybridization conditions are well-known in the art. Stringent conditions are sequence-dependent and will be different under different circumstances. Generally, stringent conditions are selected to be about 5° C. lower than the thermal melting point (Tm) for the specific sequence under defined conditions of pH and ionic strength at which 50% of the base pairs are dissociated.

The term "substantially complementary" as used herein means sequences that are complementary except for minor regions of mismatches. Typically, the total number of mismatches in a nucleic acid that is about 15 nucleotides in length is about 3 nucleotides or less.

The term "target sequence" and "target region" as used herein means a region of a nucleic acid that it to be detected, or detected and analyzed, and comprises the polymorphic site of interest.

The term "test sample," "biological sample," "patient sample," or "sample" as used herein means a sample taken from a subject, or a biological fluid, wherein the sample may contain a KRAS target sequence. A test sample may be taken from any source, for example, tissue, blood, plasma, saliva, sputa, mucus, sweat, urine, urethral swabs, cervical swabs, urogenital or anal swabs, conjunctival swabs, ocular lens fluid, cerebral spinal fluid, etc. A test sample may be used (i) directly as obtained from the source or (ii) following a pre-treatment to modify the character of the sample. Thus, a test sample can be pre-treated by, for example, preparing plasma or serum from blood, disrupting cells or viral particles, preparing liquids from solid materials, diluting viscous fluids, filtering liquids, adding reagents, purifying nucleic acids, etc. In some embodiments, the sample may be formalin-fixed paraffin-embedded (FFPE) tissue. In other embodiments, the sample may be nucleic acid (e.g., DNA and/or RNA) extracted or obtained from FFPE tissue. In still other embodiments, the sample may be nucleic acid (e.g., DNA and/or RNA) extracted or obtained from blood, plasma, or another body fluid.

The term "treat," "treating," or "treatment" as used herein interchangeably means to reverse, alleviate, or inhibit the progress of a disease, or one or more symptoms of such disease, to which such term applies. Depending on the condition of the subject, the term also refers to preventing a disease, and includes preventing the onset of a disease, or preventing symptoms associated with a disease. A treatment may be either performed in an acute or chronic way. The term also refers to reducing the severity of a disease or symptoms associated with such disease prior to affliction with the disease. "Preventing" also refers to preventing the recurrence of a disease with one or more symptoms associated with such disease. "Treatment" and "therapeutically" refer to the act of treating as "treating" is defined above.

The terminology used herein is for the purpose of describing particular embodiments only and is not otherwise intended to be limiting. For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHOD OF IDENTIFYING SINGLE NUCLEOTIDE POLYMORPHISMS IN KRAS

Provided herein is a method of identifying one or more single nucleotide polymorphisms (SNPs) in v-Ki-ras2 Kirsten rat sarcoma viral oncogene homolog (KRAS) in a subject in need thereof. The method of identifying determines the presence or absence of the one or more SNPs in KRAS. The one or more SNPs in KRAS may be associated with a cancer, for example, but not limited to, a colorectal cancer (CRC) and a non-small cell lung cancer (NSCLC) as described below in more detail. The presence or absence of the one or more SNPs in KRAS may be indicative of a response of a subject suffering from a cancer (e.g., CRC or NSCLC) to a particular cancer therapy or treatment, and thus, aide in the selection of a cancer therapy for the subject.

The method of identifying distinguishes one SNP in KRAS from another SNP in KRAS. The method identifying distinguishes a SNP in KRAS from a wild-type sequence in KRAS. The method of identifying provides a sensitivity of at least about 0.01%, 0.05%, 0.1%, 0.5%, 1%, 2%, 3%, 4%, 5%, 6%, 7%, 8%, 9%, or 10% KRAS mutation in 100 ng, 10 ng, 1 ng, 1 µg, 10 µg, or 100 µg of KRAS target sequence. The method of identifying provides a sensitivity of at least about 0.01%, 0.05%, 0.1%, 0.5%, 1%, 2%, 3%, 4%, 5%, 6%, 7%, 8%, 9%, or 10% KRAS mutation in 10 ng of KRAS target sequence. In some embodiments, the method provides a sensitivity of at least about 2% KRAS mutation in 10 ng of KRAS target sequence.

The method of identifying is reproducible. The method of identifying provides at least about 90%, 91%, 92%, 93%, 94%, 95%, 96%, 97%, 98%, 99%, or 100% reproducibility in the detection of the presence or absence of the one or more SNPs. In some embodiments, the method of identifying provides 100% reproducibility in the detection of the presence or absence of the one or more SNPs.

The method of identifying is specific for the one or more SNPs targeted for detection, thereby avoiding cross-reactivity with or interference from contaminating and/or interfering substances such as microorgansims, hemoglobin, triglycerides, necrotic tissue, and so forth, which may be present in a sample obtained from the subject. The method of identifying is specific for the one or more SNPs in KRAS targeted for detection, and thus, does not cross-react with homologs of KRAS, for example, hRAS and nRAS, and the KRAS pseudogene KRAS1P.

The method includes obtaining a sample from the subject, in which the sample may or may not include a KRAS target sequence. As described below in more detail, the KRAS target sequence may be a wild-type KRAS sequence, a mutant KRAS sequence, or a combination thereof.

The method also includes measuring or detecting the one or more SNPs in KRAS. Measuring or detecting may include forming a reaction mixture as described below in more detail. The reaction mixture may include primers for amplifying the KRAS target sequence (or a portion thereof) and a peptide nucleic acid (PNA) oligomer. The PNA oligomer prevents the amplification of a wild-type KRAS sequence, thereby allowing for the selective amplification of a mutant KRAS sequence. This selective amplification enriches for the amplified mutant KRAS sequence. Accordingly, the mutant KRAS sequence, if present in the sample, is selectively amplified (and thus enriched for) regardless of whether the subject from whom the sample was obtained was heterozygous or homozygous for the one or more SNPs in KRAS. This selective amplification also provides the advantageous properties of requiring less sample for the detection of the one or more SNPs in KRAS, and less interference or noise due to the amplification of the wild-type KRAS sequence.

The reaction mixture may also include an internal control. The reaction mixture may further include one or more probes, each allowing for the independent detection, and thus identification, of a different SNP in KRAS. The one or more probes may be detectably labeled as described below in more detail.

The method also includes subjecting the reaction mixture to conditions sufficient for the formation of one or more amplicons that contain the one or more SNPs in KRAS. The method further includes detecting the one or more amplicons with the one or more probes, in which detection signals the presence of the one or more SNPs in KRAS. No detection signals the absence of the one or more SNPs in KRAS. Detection may be aligned to a particular SNP in KRAS.

Advantageously, the one or more probes may each be independently labeled with a different label, thereby allowing for the detection, and thus identification, of more than one SNP in KRAS. In some embodiments, probes that detect different mutations within a respective codon, in which the different mutations give rise to the same amino acid substitution, may contain the same label. Specifically, multiple SNPs (e.g., 1, 2, 3, 4, 5, 6, 7, 8, 9, 10, 11, 12, 13, 14, 15, 16, 17, 18, 19, 20, or more SNPs) may be detected and identified in a simultaneous manner with the method of identifying described herein. This provides the advantageous capability of determining the presence or absence of about 98%, about 97%, about 96%, about 95%, about 94%, about 93%, about 92%, about 91%, about 90% of the mutations in KRAS that are associated with CRC and NSCLC, respectively, with a small amount of sample input (such as 1 ng, 10 ng, 100 ng, or 1 µg) given the enrichment provided by the selective amplification of mutant KRAS sequences. Accordingly, the method of identifying the one or more SNPs in KRAS achieves the remarkable technical effect of detecting nearly all of the mutations in KRAS associated with CRC and NSCLC. The method of identifying also achieves the remarkable technical effect of identifying which mutations are absent and which mutations are present in the KRAS gene of a given subject. Knowing which mutations are present or absent in the KRAS gene allows a user of the method to predict the response of a subject suffering from CRC or NSCLC to a given treatment. This prediction, in turn, allows the user to select and administer an appropriate treatment as described below in more detail.

a. SNPs in the KRAS Gene

The method identifies the presence or absence of the one or more SNPs in the gene v-Ki-ras2 Kirsten rat sarcoma viral oncogene homolog (KRAS). KRAS encodes a small GTPase that cycles between a GTP-bound active conformation and a GDP-bound inactive conformation. The GTPase encoded by KRAS is also a member of the mitogen-activated protein kinase (MAPK) signaling pathway, which regulates cell proliferation and differentiation. Specifically, KRAS is activated by upstream signals that originated from cell surface receptor tyrosine kinases (RTKs), for example, epidermal growth factor receptor (EGFR). The active conformation of KRAS propagates the signals by activating downstream rapidly accelerated fibrosarcoma (RAF) kinases, for example, B-RAF.

Mutations in KRAS that prohibit GTP hydrolysis are oncogenic because these mutations induce a constitutively active KRAS conformation. These activating mutations are predominantly located within codons 12, 13, and 61 of the KRAS gene and can be SNPs. There are up to 18 amino acid changes possible in codons 12 and 13 of exon 2, and 61 of exon 3 of the KRAS gene. Codons 12 and 13 are located in exon 2 of the KRAS gene while codon 61 is located in exon 3 of the KRAS gene. Activating mutations in KRAS are found in several cancers including, for example, colorectal cancer (CRC) and non-small cell lung cancer (NSCLC) as described below in more detail. In particular, of the eighteen amino acid changes possible in codons 12, 13, and 61, greater than 98% of identified KRAS mutations in these cancers are G12D, G12A, G12V, G12S, G12C, G12R, G13D, G13C, or Q61H. Additionally, mutations located in codons 117 and 146 of the KRAS gene are oncogenic. There are up to four amino acid changes possible in codons 117 and 146 of the KRAS gene that are oncogenic (see Table 1 below), and may be combined with the mutation changes in codons 12, 13 and/or 61 of the KRAS gene discussed above and shown below in Table 1).

Accordingly, the one or more SNPs in KRAS may be associated with a cancer, for example, but not limited to, a colorectal cancer (CRC) and a non-small cell lung cancer (NSCLC). The presence or absence of the one or more SNPs in KRAS may be indicative of a response of a subject suffering from a cancer (e.g., CRC or NSCLC) to a particular cancer therapy or treatment as described in more detail below.

The one or more SNPs may be found in exon 2, exon3, exon 2 and exon 3, or another portion of the of the KRAS gene. The one or more SNPs may be found in codon 12, 13, 61, 117, and/or 146 of the KRAS gene. The one or more SNPs may be one or more of the SNPs listed in Table 1 below. In some embodiments, the one or more SNPs may be one or more of G12S, G12C, G12R, G12V, G12D, G12A, G13D, G13C, Q61H (i.e., Q61Ha or Q61Hb).

The one or more SNPs may be any combination of the SNPs listed in Table 1 below. In some embodiments, the one or more SNPs may be any combination of G12S, G12C, G12R, G12V, G12D, G12A, G13D, G13C, Q61H (i.e., Q61Ha or Q61Hb).

TABLE 1

| Mutation | Sequence* |
|---|---|
| Wild-type—codons 12 and 13 | GGTGGC |
| G12D | GATGGC |
| G12V | GTTGGC |
| G13D | GGTGAC |
| G12C | TGTGGC |
| G12S | AGTGGC |
| G12A | GCTGGC |
| G12R | CGTGGC |
| G13C | GGTTGC |
| G13R | GGTCGC |
| G13S | GGTAGC |

TABLE 1-continued

| Mutation | Sequence* |
|---|---|
| G13A | GGTGCC |
| G13V | GGTGTC |
| Wild-type—codon 61 | CAA or CAG |
| Q61H | CAC or CAT (also referred to herein as "Q61Ha" or "Q61Hb," respectively)** |
| Q61L | CTA |
| Q61R | CGA |
| Q61K | AAA |
| Q61P | CCA |
| Q61E | GAA |
| Wild-type—codon 117 | AAA |
| K117N | AAC or AAT |
| Wild-type—codon 146 | GCA |
| A146P | CCA |
| A146T | ACA |
| A146V | GTA |

*Underling marks the single nucleotide polymorphism giving rise to the corresponding mutation (i.e., substitution) in the amino acid sequence.
**Either Q61Ha or Q61Hb may give rise to the Q61H mutation.

(1) SNP Association with Cancer

The one or more SNPs in the KRAS gene may be associated with a cancer cell, a cancerous tissue, a cancer, a neoplasm, a tumor, and/or a metastatic cancer. In particular, the one or more SNPs in the KRAS gene described above may be associated with one or more cancers. The one or more cancers may be, but are not limited to, colorectal cancer (CRC) and non-small cell lung cancer (NSCLC).

35% of colorectal cancers or tumors include a mutation in the KRAS gene. 16% of non-small cell lung cancers or tumors include a mutation in the KRAS gene. Table 2 below shows the occurrence of each SNP in the identified cancer.

In particular, the presence or absence of one or more of the SNPs listed in Table 1 above allows a user of the method of identifying described herein to predict the response of a subject suffering from CRC or NSCLC to a given treatment. This prediction, in turn, allows the user to select and administer an appropriate treatment as described below in more detail.

In some embodiments, the presence or absence of one or more of the SNPs G12S, G12C, G12R, G12V, G12D, G12A, G13D, G13C, and Q61H allows a user of the method of identifying described herein to predict the response of a subject suffering from CRC or NSCLC to a given treatment. This prediction, in turn, allows the user to select and administer an appropriate treatment as described below in more detail.

TABLE 2

| Mutation | Percent Occurrence in CRC | Percent Occurrence in NSCLC |
|---|---|---|
| G12D | 33.99 | 17.47 |
| G12V | 22.03 | 20.05 |
| G13D | 19.21 | 2.55 |
| G12C | 8.22 | 41.29 |
| G12S | 5.97 | 4.10 |
| G12A | 6.12 | 6.68 |
| G12R | 1.23 | 2.07 |
| G13C | 0.51 | 2.70 |
| G13R | 0.25 | 0.11 |
| G13S | 0.06 | 0.22 |
| G13A | 0.09 | 0.07 |
| G13V | 0.12 | 0.07 |
| Q61H | 0.52 | 0.48 |
| Q61L | 0.18 | 0.30 |
| Q61R | 0.14 | 0.33 |
| Q61K | 0.07 | 0.18 |
| Q61P | 0.00 | 0.07 |
| Q61E | 0.01 | 0.15 |

(2) KRAS Target Sequence

The method may include the amplification of the KRAS target sequence. The KRAS target sequence may be present within DNA, RNA, or cDNA. The DNA may be genomic DNA or circulating tumor DNA (ctDNA). In some embodiments, the DNA, RNA, or cDNA may be circulating within or found in blood, plasma, or other bodily fluids.

The KRAS target sequence may be present within DNA, RNA, or cDNA obtained from a sample, which is described above. The KRAS target sequence may be present within DNA obtained from a tissue or cell from a cancer or tumor. The KRAS target sequence may be present within genomic DNA obtained from a tissue or cell from a cancer or tumor. The KRAS target sequence may be present within genomic DNA obtained or extracted from a fixed-formalin paraffin-embedded (FFPE) cancer or tumor tissue. The KRAS target sequence may be present within genomic DNA obtained from a tissue or cell from a colorectal cancer or tumor. The KRAS target sequence may be present within genomic DNA obtained from a tissue or cell from a non-small cell lung cancer or tumor. The KRAS target sequence may be present within exon 2 (first amplicon discussed below) and/or exon 3 (second amplicon as discussed below) of the KRAS sequence.

The KRAS target sequence may be the wild-type KRAS sequence, the mutant KRAS sequence, or the combination thereof. The wild-type KRAS sequence does not contain one or more of the SNPs described above. The mutant KRAS sequence may contain one or more of the SNPs described above.

(a) Primers for Amplifying Exon 2 of the KRAS Gene

The KRAS target sequence may be exon 2 (or a portion thereof) of the KRAS gene. Accordingly, the method may include a pair of primers for amplifying exon 2 (or a portion thereof) of the KRAS gene. This primer pair specifically hybridizes to nucleic acid sequences contained within exon 2 of the KRAS gene. The primer pair includes a first forward primer and a first reverse primer for the generation of a first amplicon (i.e., also known herein as the "exon 2 forward primer" and "exon 2 reverse primer", respectively). The first amplicon may include one or more of the SNPs G12S, G12C, G12R, G12V, G12D, G12A, G13C, G13D, or any combination thereof. The first amplicon may be generated simultaneously with a second amplicon and/or a third amplicon, which are described below in more detail.

The first forward primer may include or have a nucleic acid sequence as set forth in SEQ ID NO:1, SEQ ID NO:2, or SEQ ID NO:3 (see Table 3 below). The first reverse primer may include or have a nucleic acid sequence as set forth in SEQ ID NO:4, SEQ ID NO:5, or SEQ ID NO:6 (see Table 3 below).

TABLE 3

| Primer | Sequence (5' to 3') | SEQ ID NO: |
|---|---|---|
| First forward primer (i.e., exon 2 forward primer) | TGTGACATGTTCTAATATAGT CACATT | SEQ ID NO: 1 |
| | GTGTGACATGTTCTAATATAG TCACATT | SEQ ID NO: 2 |
| | GTGTGACATGTTCTAATATAG TCACA | SEQ ID NO: 3 |
| First reverse primer (i.e., exon 2 reverse primer) | GTATCGTCAAGGCACTCTTGC | SEQ ID NO: 4 |
| | GTTCTCACGGAACTGCTATGT | SEQ ID NO: 5 |
| | GTATCGTCAAGGCACTCGTGC | SEQ ID NO: 6 |

(b) Primers for Amplifying Exon 3 of the KRAS Gene

The KRAS target sequence may be exon 3 (or a portion thereof) of the KRAS gene. Accordingly, the method may include a pair of primers for amplifying exon 3 (or a portion thereof) of the KRAS gene. This primer pair specifically hybridizes to nucleic acid sequences contained within exon 3 of the KRAS gene. The primer pair includes a second forward primer and a second reverse primer for the generation of the second amplicon (i.e., also known herein as the "exon 3 forward primer" and "exon 3 reverse primer", respectively). The second amplicon may include the SNP Q61H. The second amplicon may be generated simultaneously with the first amplicon and/or the third amplicon.

The second forward primer may include or have a nucleic acid sequence as set forth in SEQ ID NO:7, SEQ ID NO:8, or SEQ ID NO:9 (see Table 4 below). The second reverse primer may include or have a nucleic acid sequence as set forth in SEQ ID NO:10, SEQ ID NO:11, or SEQ ID NO:12 (see Table 4 below).

TABLE 4

| Primer | Sequence (5' to 3') | SEQ ID NO: |
|---|---|---|
| Second forward primer (i.e., exon 3 forward primer) | CAGACTGTGTTTCTCCCTTC TCAGG | SEQ ID NO: 7 |
| | CAGACTGTGTTTCTCCCTTC TCA | SEQ ID NO: 8 |
| | CAGACTGTGTTTCTCCCTTC TCAG | SEQ ID NO: 9 |
| Second reverse primer (i.e., exon 3 reverse primer) | CTGGTCCCTCATTGCACTGT | SEQ ID NO: 10 |
| | CTGGTCCCTCATTGCACTGT | SEQ ID NO: 11 |
| | TACTGGTCCCTCATTGCACT | SEQ ID NO: 12 |

(3) Probes for the Detection of the SNPs

The method includes one or more probes for detecting the one or more SNPs in the KRAS gene as described above. The one or more probes may specifically hybridize to the first amplicon or the second amplicon. The one or more probes may contain a label, in which each probe contains a different label, thereby allowing for the independent detection of each probe. The label is described below in more detail. In some embodiments, probes that detect different mutations within a respective codon, in which the different mutations give rise to the same amino acid substitution, may contain the same label, thereby allowing for the independent detection of each probe(s) associated with a specific amino acid substitution.

As described above, the first amplicon may include one or more of the SNPs G12S, G12C, G12R, G12V, G12D, G12A, G13C, G13D, or any combination thereof. Accordingly, the one or more probes that specifically hybridize to the first amplicon may include a probe that specifically hybridizes to the first amplicon when the SNP G12S is present in the first amplicon (i.e., also known herein as "the G12S probe"), a probe that specifically hybridizes to the first amplicon when the SNP G12C is present in the first amplicon (also known herein as "the G12C probe"), a probe that specifically hybridizes to the first amplicon when the SNP G12R is present in the first amplicon (i.e., also known herein as "the G12R probe"), a probe that specifically hybridizes to the first amplicon when the SNP G12V is present in the first amplicon (i.e., also known herein as "the G12V probe"), a probe that specifically hybridizes to the first amplicon when the SNP G12D is present in the first amplicon (i.e., also known herein as "the G12D probe"), a probe that specifically hybridizes to the first amplicon when the SNP G12A is present in the first amplicon (i.e., also known herein as "the G12A probe"), a probe that specifically hybridizes to the first amplicon when the SNP G13C is present in the first amplicon (i.e., also known herein as "the G13C probe"), a probe that specifically hybridizes to the first amplicon when the SNP G13D is present in the first amplicon (also known herein as "the G13D probe"), or any combination thereof.

The G12S probe may include or have a nucleic acid sequence as set forth in SEQ ID NO:22, SEQ ID NO:23, or SEQ ID NO:24 (see Table 5 below). The G12C probe may include or have a nucleic acid sequence as set forth in SEQ ID NO:25, SEQ ID NO:26, or SEQ ID NO:27 (see Table 5 below). The G12R probe may include or a nucleic acid sequence as set forth in SEQ ID NO:28, SEQ ID NO:29, or SEQ ID NO:30 (see Table 5 below). The G12V probe may include or have a nucleic acid sequence as set forth in SEQ ID NO:19, SEQ ID NO:20, or SEQ ID NO:21 (see Table 5 below). The G12D probe may include or have a nucleic acid sequence as set forth in SEQ ID NO:13, SEQ ID NO:14, or SEQ ID NO:15 (see Table 5 below). The G12A probe may include or have a nucleic acid sequence as set forth in SEQ ID NO:16, SEQ ID NO:17, or SEQ ID NO:18 (see Table 5 below). The G13C probe may include or have a nucleic acid sequence as set forth in SEQ ID NO:34, SEQ ID NO:35, or SEQ ID NO:36 (see Table 5 below). The G13D probe may include or have a nucleic acid sequence as set forth in SEQ ID NO:31, SEQ ID NO:32, or SEQ ID NO:33 (see Table 5 below).

As described above, the second amplicon may include the SNP Q61H. Accordingly, the one or more probes that specifically hybridize to the second amplicon may include a probe that specifically hybridizes to the second amplicon when the SNP Q61Ha is present in the second amplicon (i.e., also known herein as "the Q61Ha probe"), a probe that specifically hybridizes to the second amplicon when the SNP Q61Hb is present in the second amplicon (i.e., also known herein as "the Q61Hb probe"), or the combination thereof.

The Q61Ha probe may include or have a nucleic acid sequence as set forth in SEQ ID NO:37, SEQ ID NO:38, or SEQ ID NO:39 (see Table 5 below). The Q61Hb probe may include or have a nucleic acid sequence as set forth in SEQ ID NO:40, SEQ ID NO:41, or SEQ ID NO:42 (see Table 5 below).

TABLE 5

| Probe | Sequence (5' to 3') | SEQ ID NO: |
|---|---|---|
| G12D probe | TACGCCATCAGCTC | SEQ ID NO: 13 |
| | CTACGCCATCAGCT | SEQ ID NO: 14 |
| | CTACGCCATCAGCTC | SEQ ID NO: 15 |
| G12A probe | CCAGCAGCTCCAA | SEQ ID NO: 16 |
| | CGCCAGCAGCTCC | SEQ ID NO: 17 |
| | TACGCCAGCAGCT | SEQ ID NO: 18 |
| G12V probe | TACGCCAACAGCTC | SEQ ID NO: 19 |
| | CTACGCCAACAGCT | SEQ ID NO: 20 |
| | CTACGCCAACAGCTC | SEQ ID NO: 21 |
| G12S probe | TACGCCACTAGCTC | SEQ ID NO: 22 |
| | CTACGCCACTAGCT | SEQ ID NO: 23 |
| | CTACGCCACTAGCTC | SEQ ID NO: 24 |
| G12C probe | CTACGCCACAAGCT | SEQ ID NO: 25 |
| | CTACGCCACAAGCTC | SEQ ID NO: 26 |
| | TACGCCACAAGCTC | SEQ ID NO: 27 |
| G12R probe | CTACGCCACGAGCT | SEQ ID NO: 28 |
| | CTACGCCACGAGCTC | SEQ ID NO: 29 |
| | TACGCCACGAGCTC | SEQ ID NO: 30 |
| G13D probe | TACGTCACCAGCTC | SEQ ID NO: 31 |
| | ACGTCACCAGCTCC | SEQ ID NO: 32 |
| | ACGTCACCAGCTCC | SEQ ID NO: 33 |
| G13C probe | CGCAACCAGCTCCA | SEQ ID NO: 34 |
| | ACGCAACCAGCTCCA | SEQ ID NO: 35 |
| | ACGCAACCAGCTCC | SEQ ID NO: 36 |
| Q61Ha probe | TCCTCGTGACCTGC | SEQ ID NO: 37 |
| | CCTCGTGACCTGCT | SEQ ID NO: 38 |
| | CTCCTCGTGACCTG | SEQ ID NO: 39 |
| Q61Hb probe | CTCATGACCTGCTG | SEQ ID NO: 40 |
| | ACTCCTCATGACCG | SEQ ID NO: 41 |
| | TACTCCTCATGACC | SEQ ID NO: 42 | b. Internal Control (IC)

The method also includes the internal control in the reaction mixture, formation of which is described in more detail below. The internal control is a portion of the KRAS gene with no known incidence of mutations. The internal control indicates whether conditions were sufficient for amplification to occur in the reaction mixture, and thus, indicates the efficiency of amplification. The internal control also indicates if the KRAS target sequence was present in the sample obtained from the subject. The internal control further indicates a total amount of the KRAS target sequence that was amplifiable as described below in more detail, and thus, indicates the input amount of the KRAS target sequence in the reaction mixture. Additionally, if the KRAS target sequence is extracted from the sample before amplification, the internal control may indicate the efficiency of extraction.

The internal control includes a pair of primers for generating the third amplicon and a probe for detecting the third amplicon (also known herein as "the internal control probe" or "IC probe"). Formation of the third amplicon does not interfere with the formation of the first amplicon and/or second amplicon described above. Additionally, the third amplicon may be detected simultaneously with detection of the first and/or second amplicon.

(1) Primers for the Internal Control (IC)

The internal control includes the primer pair for generating the third amplicon. This primer pair specifically hybridizes to nucleic acid sequences contained within a portion of the KRAS gene with no known incidence of mutation. Accordingly, formation of the third amplicon is independent from formation of the first and second amplicons described above, and thus, does not interfere with formation of the first and second amplicons.

This primer pair includes a third forward primer and a third reverse primer for generating the third amplicon (i.e., also known herein as the "IC forward primer" and "IC reverse primer", respectively). This third amplicon may be generated simultaneously with the second amplicon and/or the first amplicon. The third forward primer may include or have a nucleic acid sequence as set forth in SEQ ID NO:43, SEQ ID NO:44, or SEQ ID NO:45 (see Table 6 below). The third reverse primer may include or have a nucleic acid sequence as set forth in SEQ ID NO:46, SEQ ID NO:47, or SEQ ID NO:48 (see Table 6 below).

TABLE 6

| Primer | Sequence (5' to 3') | SEQ ID NO: |
| --- | --- | --- |
| Third forward primer (i.e., IC forward primer) | ATTAATGAAATTTGTTACCT GTACACATGA | SEQ ID NO: 43 |
| | TAATGAAATTTGTTACCTGT ACACATGA | SEQ ID NO: 44 |
| | ATTAATGAAATTTGTTACCT GTACACATG | SEQ ID NO: 45 |
| Third reverse primer (i.e., IC reverse primer) | ATGTTTTCGAATTTCTCGAA CTAATGT | SEQ ID NO: 46 |
| | ATGTTTTCGAATTTCTCGAA CTAATGTAT | SEQ ID NO: 47 |
| | ATGTTTTCGAATTTCTCGAA CTAATGTA | SEQ ID NO: 48 |

(2) Internal Control Probe

The internal control also includes the IC probe, which specifically hybridizes to the third amplicon. The IC probe may contain a label, which is different than the label used for the one or more probes described above (i.e., the G12S probe, G12C probe, G12R probe, G12V probe, G12D probe, G12A probe, G13C probe, G13D probe, Q61Ha probe, and/or Q61Hb probe), thereby allowing for independent and simultaneous detection of the IC probe and the one or more probes that specifically hybridize to the first or second amplicons. The IC probe may include or have a nucleic acid sequence as set forth in SEQ ID NO:49, SEQ ID NO:50, or SEQ ID NO:51 (see Table 7 below).

TABLE 7

| Probe | Sequence (5' to 3') | SEQ ID NO: |
| --- | --- | --- |
| IC probe | GCCATCGTATATATTCACATT | SEQ ID NO: 49 |
| | CCATCGTATATATTCACATTTA | SEQ ID NO: 50 |
| | CCATCGTATATATTCACATT | SEQ ID NO: 51 | c. PNA Oligomer

The method includes the use of the PNA oligomer to block amplification of the wild-type KRAS sequence, thereby allowing for the selective amplification and enrichment of the mutant KRAS sequence. The PNA oligomer is complementary to, and thus selectively hybridizes to, the wild-type KRAS sequence. In particular, the PNA oligomer selectively hybridizes to a nucleic acid sequence in the wild-type KRAS sequence that is located downstream of where the first or second forward primer or the first or second reverse primer selectively hybridizes to the KRAS target sequence (FIG. 1). As such, the PNA oligomer blocks extension of the first or second forward primer or the first or second reverse primer. For example, as shown in FIG. 1, the PNA oligomer blocks extension of the reverse primer, however, it should be understood, that the PNA oligomer may be designed to hybridize to either strand of the KRAS target sequence, and thus, block extension from either a forward primer or a reverse primer.

The PNA oligomer blocks primer extension because duplexes formed from the complementary strands of PNA and target sequence (e.g., DNA) have greater thermal stability than the corresponding DNA:DNA duplexes and thus, are not readily dislodged by an elongating polymerase. The PNA:DNA duplex, however, can be destabilized by a single mismatch and dislodged by the elongating polymerase. Accordingly, when the KRAS target sequence is the wild-type KRAS sequence, the PNA oligomer selectively hybridizes to the wild-type KRAS sequence, the PNA:DNA duplex is formed, and elongation is arrested, thereby blocking or preventing formation of an amplicon from the wild-type KRAS sequence.

When the KRAS target sequence is the mutant KRAS sequence, one or more mismatches occurs in the PNA:DNA duplex, thereby destabilizing the PNA:DNA duplex. Elongation can proceed through the destabilized duplex, resulting in the generation of an amplicon from the mutant KRAS sequence.

Accordingly, the PNA oligomer provides for the selective amplification, and thus enrichment, of the mutant KRAS sequence. Therefore, the mutant KRAS sequence, if present in the sample, is selectively amplified (and thus enriched for) regardless of whether the subject from whom the sample was obtained was heterozygous or homozygous for the one or more SNPs in KRAS. This selective amplification also provides the advantageous properties of requiring less sample for the detection of the one or more SNPs in KRAS and less interference or noise due to the amplification of the wild-type KRAS sequence. This reduced interference, in turn, facilitates the simultaneous detection and identification of multiple SNPs (e.g., 1, 2, 3, 4, 5, 6, 7, 8, 9, 10, 11, 12, 13, 14, 15, 16, 17, 18, 19, 20, or more SNPs) in the KRAS gene. This simultaneous detection and identification achieves the remarkable technical effect of detecting nearly all of the mutations in KRAS associated with CRC and NSCLC and identifying which of these mutations are absent and/or present in the KRAS gene of a given subject.

The PNA oligomer may selectively hybridize to the first amplicon described above. The PNA oligomer may selectively hybridize to the second amplicon described above. The PNA oligomer may be two PNA oligomers, one of which selectively hybridizes to the first amplicon and the other of which selectively hybridizes to the second amplicon.

The PNA oligomer may include or have a sequence as set forth in SEQ ID NO:52, SEQ ID NO:53, SEQ ID NO:54, SEQ ID NO:55, SEQ ID NO:56, or SEQ ID NO:57 (see Table 8 below). The PNA oligomer that has the sequence as set forth in SEQ ID NO:52, SEQ ID NO:53, or SEQ ID NO:54 may selectively hybridize to the first amplicon (i.e., the amplified region of exon 2 of the KRAS gene), and thus, may also be known herein as the "exon 2 PNA oligomer". The PNA oligomer that has the sequence as set forth in SEQ ID NO:55, SEQ ID NO:56, or SEQ ID NO:57 may selectively hybridize to the second amplicon (i.e., the amplified region of exon 3 of the KRAS gene), and thus, may also be known herein as the "exon 3 PNA oligomer".

TABLE 8

| PNA Oligomer | Sequence (N-terminal to C-terminal) | SEQ ID NO: |
|---|---|---|
| Exon 2 PNA oligomer | CCTACGCCACCAGCTCC | SEQ ID NO: 52 |
| | TGCCTACGCCACCAGC | SEQ ID NO: 53 |
| | GCCTACGCCACCAGC | SEQ ID NO: 54 |
| Exon 3 PNA oligomer | ACTCCTCTTGACCTGCT | SEQ ID NO: 55 |
| | CTCCTCTTGACCTGCTGTG | SEQ ID NO: 56 |
| | ACTCCTCTTGACCTGCTG | SEQ ID NO: 57 | d. Primer and Probe Sets

The method of identifying may utilize any combination of the above described primers, probes, and PNA oligomers in a primer and/or probe set. The primer set may include, but is not limited to, (1) SEQ ID NOS:2 and 6; (2) SEQ ID NOS:7 and 11; (3) SEQ ID NOS:43 and 48; (4) SEQ ID NOS:2, 6, 7, and 11; (5) SEQ ID NOS:2, 6, 7, 11, 43, and 48; (6) SEQ ID NOS:7, 11, 43, and 48; and (7) SEQ ID NOS:2, 6, 43, and 48. In some embodiments, the primer set may further include SEQ ID NO:52, SEQ ID NO:56, or SEQ ID NOS:52 and 56.

The primer and probe set may include, but is not limited to, (1) SEQ ID NOS:2, 6, 43, 48, 22, 27, 30, and 51; (2) SEQ ID NOS:2, 6, 43, 48, 13, 16, 20, and 51; and (3) SEQ ID NOS:2, 6, 7, 11, 43, 48, 31, 34, 38, 40, and 51. The primer and probe set may further include SEQ ID NO:52, SEQ ID NO:56, or SEQ ID NOS:52 and 56.

In other embodiments, the primer and probe set may include, but again is not limited to, (1) SEQ ID NOS:2, 6, 43, 48, 13, 16, 20, 22, 27, 30, and 51; (2) SEQ ID NOS:2, 6, 43, 48, 13, 16, 20, 22, 27, 30, 31, 34, and 51 (3) SEQ ID NOS:2, 6, 7, 11, 43, 48, 13, 16, 20, 22, 27, 30, 31, 34, 38, 40, and 51. The primer and probe set may further include SEQ ID NO:52, SEQ ID NO:56, or SEQ ID NOS:52 and 56.

In some embodiments, the primer and probe set may include any combination of the primers, probes, and PNA oligomers described above in Tables 3, 4, 5, 6, 7, and 8.

e. Chemical Modification of Primers

The method of identifying the one or more SNPs in KRAS may use chemically modified versions of the above-described primers, for example, to improve the efficiency of hybridization to the KRAS target sequence. For example, because variation (due to codon wobble in the third position) in conserved regions among species often occurs in the third position of a DNA triplet, the primers described above may be modified such that the nucleotide corresponding to this position is a "universal base" that can bind to more than one nucleotide. For example, inosine (I) binds uridine (U), cytosine (C), or adenine (A), guanine (G) binds to U or C, and U binds to A or G. Other examples of universal bases include nitroindoles such as 5-nitroindole or 3-nitropyrrole, the degenerate nucleotides dP or dK, an acyclic nucleoside analog containing 5-nitroindazole or the purine analog 1-(2-deoxy-β-D-ribofuranosyl)-imidazole-4-carboxamide.

In another embodiment, to compensate for the somewhat weaker binding by the "wobble" base, the primers may be designed such that the first and second positions of each triplet are occupied by nucleotide analogs which bind with greater affinity than the unmodified nucleotide. Examples of these analogs include 2,6-diaminopurine, which binds to thymine, propyne T, which binds to adenine, and propyne C and phenoxazines, including G-clamp, which bind to guanine Propynylated pyrimidines are described in U.S. Pat. Nos. 5,645,985, 5,830,653, and 5,484,908, the entire contents of each patent are herein incorporated by reference. Phenoxazines are described in U.S. Pat. Nos. 5,502,177, 5,763,588, and 6,005,096, the entire contents of each patent are herein incorporated by reference. G-clamps are described in U.S. Pat. Nos. 6,007,992 and 6,028,183, the entire contents of each patent are herein incorporated by reference.

f. Labels

The method of identifying the one or more SNPs in KRAS may use a label for the above-described probes to facilitate their detection (i.e., the probes are detectably labeled). The method of identifying may also use a quencher in combination with this label, when it is a fluorescent label, as described below in more detail for the above-described probes.

The label may be detected by spectroscopic, photochemical, biochemical, immunochemical or chemical means known to those skilled in the label detection arts. The label may be a fluorophore or fluorescent label, a chemiluminescent label, or another moiety that has affinity for another molecule. Other useful labels include a dye, such as a fluorescent dye, a radioactive label, such as $^{32}P$, an electron-dense reagent, an enzyme, such as peroxidase or alkaline phosphatase, biotin, or haptens and proteins for which antisera or monoclonal antibodies are available.

Fluorophores of different colors may be chosen such that each probe in the reaction mixture can be distinctly detected. For example, a combination of the following fluorophores may be used (but is not limited to): FAM™ (Life Technologies, Carlsbad, Calif.), VIC® (Life Technologies, Carlsbad, Calif.), Cy®5 (Molecular Probes, Inc., Eugene, Oreg.), NED™ (Life Technologies, Carlsbad, Calif.), 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxyamido] hexanoic acid, N-(4,4-difluoro-5,7-dimethyl-4-bora-3a,4a diaza-3-indacenepropionic acid, eosin-5-isothiocyanate, erythrosine-5-isothiocyanate, Cascade™ blue acetylazide (Molecular Probes, Inc., Eugene, Oreg.), the Violet/Blue dyes (Emmax 375-491 nm) 7-methoxycoumarin-3-carboxy, AMCA-X (7-aminocoumarin-X), 6-MI or 6-MAP (6-methyl-8-(2-deoy-(3-D-ribofuranosyl)isoxanthopteridine); the Green/Yellow dyes (Emmax 492-585 nm) DTAF (4,6-dichlorotriazinyl)aminofluorescein, 6-FAM (fluorescein, 6-carboxyfluorescein), Dansyl-X (6-((5-dimethtylaminonaphtalene-1-sulfonyl)amino)hexanoate, 6-JOE (6-carboxy-4',5'-dichloro-2',7'-dimethoxyfluorescein), HEX (hexachlorofluorescein), BODIPY-TMR-X (tetramethylrhodamine substitute), PyMPO (1-(3-carboxybenzyl)-4-(5-(4-methoxyphenyl)oxazol-2-yl)pyridinium bromide), TAMRA-X (6-(tetramethylrhodamine-5(6)-carboxamido)hexanoate); the Orange dyes (Emmax 586-647 nm) rhodamine derivatives BODIPY 576/589, BODIPY 581/591, ROX (carboxyrhodamine), VIC (Applied Biosystems Inc., Foster City, Calif.), NED (Applied Biosystems Inc., Foster City, Calif.) and the Red dyes (Emmax 647-700 nm) as carboxynaphthofluorescein.

In some embodiments, the combination of fluorophores used to label the probes in the reaction mixture may be FAM™ (Life Technologies, Carlsbad, Calif.), VIC® (Life Technologies, Carlsbad, Calif.), Cy®5 (Molecular Probes, Inc., Eugene, Oreg.), and NED™ (Life Technologies, Carlsbad, Calif.) such that each probe in the reaction mixture provides for the distinct detection and identification of its corresponding SNP in the KRAS gene.

Other molecules having fluorescent properties are also suitable labels. For example, a protein like phycoerythrin, a 240 kiloDalton (kDa) protein, displays robust fluorescent properties. Other labels having fluorescent properties may include quantum dots, nanocrystals, and related semiconductor fluorophores.

Fluorescent labels are detected by any suitable means of detecting fluorescence. Such techniques are well known in the art.

The fluorophore or fluorescent label may be used in combination with a quencher (also known herein as a "quencher moiety"). A quencher as used herein is a moiety that decreases the light emitted by the fluorophore at the wavelength at which signal is measured, or is a fluorescent moiety that serves to shift the wavelength of light emitted by the fluorophore of the nucleic acid probe. Quenchers suitable in the context of the present invention include (without limitation) DABCYL (4-(4'-dimethylaminophenylazo)benzoic acid), QSY-7 (9-[2-[[4-[[(2,5-dioxo-1-pyrrolidinyl) oxy]carbonyl]-1-piperidinyl]sulfonyl]phenyl]-3,6-bis(methylphenylamino)), BHQ-1, BHQ-2, BHQ-3 (Biosearch Technologies Inc., 2003, Cat. Nos. BG5-5041T, BG5-5042T, and BG5-5043T) and TAMRA ((6-tetramethylrhodamine-5(6)-carboxamido)hexanoate). Additionally, a quencher can be an organic dye, which may or may not be fluorescent, depending on the embodiment of the invention.

In some embodiments, the label may be a chemiluminescent label. For example, the chemiluminescent label may be, but is not limited to, acridinium compounds. Acridinium compounds may include acridinium-9-carboxamides and acridinium-9-carboxylate aryl esters. Such compounds are described, for example, in U.S. Pat. No. 5,783,699, the entire contents of which are hereby incorporated by reference.

Probes may also be indirectly labeled with biotein or digoxygenin, or labeled with radioactive isotopes such as $^{32}P$ and $^{3}H$, although secondary detection molecules or further processing then is required to detect the probes. For example, a probe indirectly labeled with biotin may be detected by avidin conjugated to a detectable marker. For example, avidin may be conjugated to an enzymatic marker such as alkaline phosphatase or horseradish peroxidase. Enzymatic markers can be detected in standard colorimetric reactions using a substrate and/or catalyst for the enzyme. Catalysts for alkaline phosphatase include 5-bromo-4-chloro-3-indolylphosphate and nitro blue tetrazolium. Diaminobenzoate may be used as a catalyst for horseradish peroxidase.

g. Positive and Negative Controls

The method of identifying may employ positive and negative controls to facilitate monitoring of sample preparation, amplification, and detection, all of which are described below in more detail. Monitoring may also include monitoring for contamination.

In some embodiments, the positive control may be designed to generate and detect an amplicon for each primer pair in the reaction mixture. For example, the positive control may include a plasmid encoding for the internal control and one or more plasmids encoding for the one or more SNPs. Additionally, if fluorescent labels are contained within the one or more probes, then the positive control may further include generation of at least one positive signal in each fluorescent channel being used to monitor amplification.

The negative control may be designed to generate and detect the third amplicon (i.e., amplification of the internal control), but not generate and detect an amplicon corresponding to the one or more SNPs. For example, the negative control may include a plasmid encoding for the internal control.

h. Sample Preparation

The method of identifying the one or more SNPs in KRAS may include obtaining a sample from the subject. In the method of identifying, the sample obtained from the subject may optionally be treated, processed, or prepared before forming the reaction mixture described below. Such treatment may include, but is not limited to, dilution, ultrafiltration, extraction, precipitation, dialysis, enzymatic digestion, and homogenization. Moreover, if such treatment methods are employed with the sample, such treatment methods have the KRAS target sequence that remains in the sample at a concentration proportional to that in an untreated sample (e.g., namely, a sample that is not subjected to any such treatment method(s)).

For example, the sample may be prepared for an amplification assay using any suitable method as is known in the art. Desirably, the method extracts and concentrates nucleic acids. The method also desirably makes the KRAS target sequence accessible for amplification, and removes potential inhibitors of amplification from the extract.

In some embodiments, the KRAS target sequence may be DNA. DNA can be isolated from peripheral blood using, for example, a DNeasy DNA isolation kit, a QIAamp DNA blood kit, or a PAXgene blood DNA kit from Qiagen Inc. (Valencia, Calif.), or other methods known to one of ordinary skill in the art. DNA from other tissue samples also can be obtained using a DNeasy DNA isolation kit. Any other DNA extraction and purification technique also can be used, including liquid-liquid and solid-phase techniques ranging from phenol-chloroform extraction to automated magnetic bead nucleic acid capture systems. RNA can be isolated and reverse-transcribed and the resulting cDNA can be amplified (e.g., reverse-transcription polymerase chain reaction (RT-PCR) as described in U.S. Pat. Nos. 5,310,652; 5,322,770; 5,561,058; 5,641,864; and 5,693,517, for example).

In other embodiments, DNA may be extracted from a fixed-formalin paraffin-embedded (FFPE) tissue. Accordingly, another example of a sample preparation kit is the QIAamp DNA FFPE tissue kit, which is available from Qiagen.

In still other embodiments, the Abbott mSample Preparation SystemDNA (4×24 preps; Abbott) reagents capture the nucleic acids and remove unbound sample components. Proteinase K is included in the lysis step to digest proteins associated with the samples. The bound nucleic acids are eluted and transferred to a 96-well deep plate. The nucleic acids are then ready for amplification. In some embodiments, an unrelated DNA sequence, which serves as an internal control (IC) to demonstrate that the process has proceeded correctly for each sample, is introduced into the sample preparation procedure and is processed along with the calibrators, controls, and specimens.

In some embodiments, if the KRAS target sequence is RNA, then reverse transcription may be used to generate cDNA. This cDNA may then be amplified in the reaction mixture as described below.

In some embodiments, the use of an automated sample preparation system, such as an automated sample preparation system designed to use magnetic microparticle processes for the purification of nucleic acids, can be preferred. An example of an automated sample preparation system is m2000sp, which is available from Abbott Laboratories, Abbott Park, Ill. Alternatively, samples can be prepared using the m24sp automated sample preparation system (Abbott) or prepared manually. Automated sample preparation is preferred over manual preparation because it is more consistent.

i. Forming a Reaction Mixture

The method of identifying the one or more SNPs in KRAS includes forming the reaction mixture. The reaction mixture comprises the sample suspected of containing the KRAS target sequence, primers for generating the first and/or second amplicons, the one or more probes for detecting the one or more SNPs in the KRAS gene, the PNA oligomer, and the internal control. The reaction mixture, upon formation, is placed under conditions sufficient for the amplification of nucleic acid sequences as described in more detail below.

Forming the reaction mixture may include forming one or more reaction mixtures. Forming the reaction mixture may include forming 1, 2, 3, 4, 5, 6, 7, 8, 9, 10, 11, 12, 13, 14, 15, 16, 17, 18, 19, 20, or more reaction mixtures. Each reaction mixture may contain a different combination of the primers for generating the first and/or second amplicons and the one or more probes for detecting the one or more SNPs in the KRAS gene. These different combinations result in the detection of unique groups of SNPs in the respective reaction mixtures. Each unique group of SNPs may include overlapping SNPs such that the generation of a single amplicon allows for the detection of the presence or absence of multiple SNPs. For example, generation of the first amplicon allows for the detection of the presence or absence of the overlapping SNPs G12C, G12R, G12S, G12D, G12A, and G12V. In another example, generation of the first amplicon allows for the detection of the presence or absence of the overlapping SNPs G13D and D13C.

The reaction mixture may also include nucleic acid amplification reagents. The nucleic acid amplification reagents may include enzymes having polymerase activity (e.g., DNA polymerase), enzyme co-factors such as magnesium or manganese, salts, and nicotinamide adenine dinucleotide (NAD), and deoxynucleotide triphosphates (dNTPs), namely dATP, dGTP, dCTP, and dTTP. In some instances, the nucleic acid amplification reagents may include ribonucleoside triphosphates.

(1) Three Reaction Mixtures for the Detection and Identification of Nine SNPs in the KRAS Gene As a non-limiting example of forming one or more reaction mixtures, forming the reaction mixture may include forming three reaction mixtures, namely a first reaction mixture, a second reaction mixture, and a third reaction mixture. These three reaction mixtures facilitate the simultaneous amplification, detection, and identification of nine different SNPs in the KRAS gene from the sample obtained from the subject. This simultaneous amplification, detection, and identification achieves the remarkable technical effect of detecting nearly all of the mutations in KRAS associated with CRC and NSCLC and identifying which of these mutations are absent and/or present in the KRAS gene of a given subject.

Figure 2:
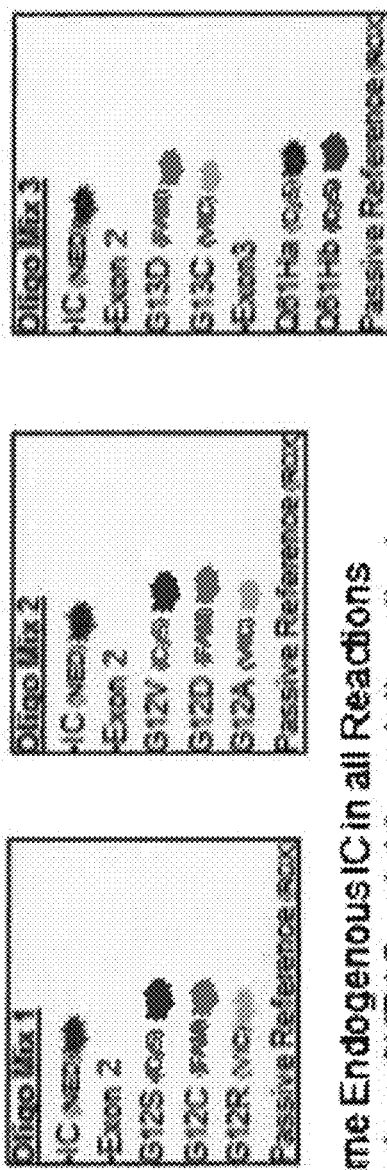
FIG. 2 shows a schematic illustrating three reaction mixtures formed by the method described herein and for the detection of nine different SNPs in the KRAS gene, namely G12S, G12C, G12R, G12V, G12D, G12A, G13D, G13C, and Q61H (i.e., Q61Ha and Q61Hb).

The first reaction mixture may include the sample suspected of containing the KRAS target sequence, primers for generating the first amplicon, three probes for detecting three SNPs in the KRAS gene, the exon 2 PNA oligomer, and the internal control. The first reaction mixture may also include the nucleic acid amplification reagents described above. In some embodiments, the first reaction mixture may include the G12C probe, the G12R probe, and the G12S probe. Each probe as well as the IC probe may have a different label, thereby allowing for independent and simultaneous detection of each probe, and thus, each of SNPs G12C, G12R, and G12S (FIGS. 2 and 3). In some embodiments (as shown in FIGS. 2 and 3), the IC probe may contain the label NED™ (Life Technologies, Carlsbad, Calif.), the G12S probe may contain the label Cy®5 (Molecular Probes, Inc., Eugene, Oreg.), the G12C probe may contain the label FAM™ (Life Technologies, Carlsbad, Calif.), and the G12R probe may contain the label VIC® (Life Technologies, Carlsbad, Calif.). In other embodiments, when each probe contains a fluorescent label, each probe may also contain the quencher, which may be for example, but is not limited, BHQ1 for use with FAM and VIC fluorescent labels, and BHQ2 for use with Quasara, Q670, and NED fluorescent labels.

The second reaction mixture may include the sample suspected of containing the KRAS target sequence, primers for generating the first amplicon, three probes for detecting three SNPs in the KRAS gene, in which the three probes are different from the three probes in the first reaction mixture, the exon 2 PNA oligomer, and the internal control. The second reaction mixture may also include the nucleic acid amplification reagents described above. In some embodiments, the second reaction mixture may include the G12D probe, the G12A probe, and the G12V probe. Each probe as well as the IC probe may have a different label, thereby allowing for independent and simultaneous detection of each probe, and thus, each of SNPs G12D, G12A, and G12V (FIGS. 2 and 3). In some embodiments (as shown in FIGS. 2 and 3), the IC probe may contain the label NED™ (Life Technologies, Carlsbad, Calf.), the G12D probe may contain the label FAM™ (Life Technologies, Carlsbad, Calif.), the G12A probe may contain the label VIC® (Life Technologies, Carlsbad, Calf.), and the G12V probe may contain the label Cy®5 (Molecular Probes, Inc., Eugene, Ore.). In other embodiments, when each probe contains a fluorescent label, each probe may also contain the quencher, which may be for example, but is not limited, BHQ1 for use with FAM and VIC fluorescent labels, and BHQ2 for use with Quasara, Q670, and NED fluorescent labels.

The third reaction mixture may include the sample suspected of containing the KRAS target sequence, primers for generating the first amplicon, primers for generating the second amplicon, four probes for detecting four SNPs in the KRAS gene, in which the four probes are different from the probes in the first and second reaction mixtures, the exon 2 PNA oligomer, the exon 3 PNA oligomer, and the internal control. The third reaction mixture may also include the nucleic acid amplification reagents described above. In some embodiments, the third reaction mixture may include the G13D probe, the G13C probe, the Q61Ha probe, and the Q61Hb probe. Each probe as well as the IC probe may have a different label, thereby allowing for independent and simultaneous detection of each probe, and thus, each of SNPs G13D, G13C, and Q61H. In some embodiments, the Q61Ha probe and the Q61Hb probe may contain the same label as both probes provide detection of the same SNP, namely Q61H. In some embodiments (as shown in FIGS. 2 and 3), the IC probe may contain the label NED™ (Life Technologies, Carlsbad, Calif.), the G13D probe may contain the label FAM™ (Life Technologies, Carlsbad, Calif.), the G13C probe may contain the label VIC® (Life Technologies, Carlsbad, Calif.), the Q61Ha probe may contain the label Cy®5 (Molecular Probes, Inc., Eugene, Oreg.), and the Q61Hb probe may contain the label Cy®5 (Molecular Probes, Inc., Eugene, Oreg.). In other embodiments, when each probe contains a fluorescent label, each probe may also contain the quencher, which may be for example, but is not limited, BHQ1 for use with FAM and VIC fluorescent labels, and BHQ2 for use with Quasar, Q670, and NED fluorescent labels.

j. Amplification

Upon formation of the reaction mixture described above, the reaction mixture is subjected to conditions sufficient for amplification of nucleic acid sequences (i.e., amplification conditions). These amplification conditions are such that a least one copy of a nucleic acid sequence complementary to the target sequence is generated if the target sequence is present in the sample. Accordingly, subjecting the reaction mixture to the amplification conditions may be repeated any suitable number of times prior to, or simultaneously with, a detection step. For example, by thermal cycling the reaction mixture between 10 and 100 times (or more), typically between about 20 and about 60 times, and more typically between about 25 and about 45 times.

The amplification conditions may include those conditions that promote the annealing and extension of one or more nucleic acid sequences. Such annealing is dependent in a rather predictable manner on several parameters, including temperature, ionic strength, sequence length, complementarity, and G:C content of the nucleic acid sequences. For example, lowering the temperature in the environment of complementary nucleic acid sequences promotes annealing. Typically, diagnostic applications use hybridization (i.e., annealing) temperatures that are about 2° C. to about 18° C. (e.g., about 10° C.) below the melting temperature, $T_m$. Ionic strength also impacts $T_m$. Typical salt concentrations depend on the nature and valency of the cation, but are readily understood by those skilled in the art. Similarly, high G:C content and increased sequence length stabilize duplex formation and increases $T_m$.

Finally, the hybridization temperature may be selected close to or at the $T_m$ of the primers. Thus, obtaining suitable hybridization conditions for a particular pair of primers or primer set is within the ordinary skill of the PCR arts.

Amplification may be carried out as known in the art, such as by use of the m2000rt instrument (Abbott Molecular Inc., Des Plaines, Ill.). The target nucleic acid (e.g., DNA, RNA or both) is amplified by DNA polymerase or reverse transcriptase in the presence of deoxynucleotide triphosphates (dNTPs) and an activation agent, for example, magnesium or manganese. During PCR amplification, high temperature is used to separate the strands of double-stranded DNA. When the reaction mixture is cooled to a temperature where DNA annealing can occur, the analyte-specific, single-stranded DNA oligonucleotide primers bind to the analyte DNA. The primers are extended by DNA polymerase, thereby making an exact copy of a short target stretch of the analyte DNA. The DNA polymerase can be, but need not be, a thermophilic enzyme that has been modified in its active site by a molecule that renders it inactive. When the enzyme is heated prior to the initiation of PCR, the inhibitory molecule is cleaved from the enzyme, thereby allowing it to regain its activity. In this manner, the enzyme is only active at temperatures where specific DNA-DNA interactions occur. This greatly reduces non-specific PCR artifacts, such as primer dimers. During each round of thermal cycling, amplification products (i.e., amplicons) dissociate to single strands at high temperature, allowing primer annealing and extension as the temperature is lowered. Exponential amplification of the target is achieved through repeated cycling between high and low temperatures. Amplification of the KRAS target sequence to generate the first, second, and/or third amplicons occurs simultaneously.

Amplification procedures are well-known in the art and include the polymerase chain reaction (PCR), real-time PCR, quantitative PCR, PNA clamp-mediated PCR, transcription-mediated amplification (TMA), rolling circle amplification, nucleic acid sequence based amplification (NASBA), ligase chain reaction, and strand displacement amplification (SDA). One skilled in the art understands that for use in certain amplification techniques, the primers may need to be modified. For example, SDA primers usually comprise additional nucleotides near the 5' ends that constitute a recognition site for a restriction endonuclease. For NASBA, the primers may include additional nucleotides near the 5' end that constitute an RNA polymerase promoter. Polynucleotides thus modified are considered to be within the scope of the present invention.

Following amplification, it may be desirable to separate the amplification product from the target sequence and the excess primer to determine whether specific amplification occurred. Separation can be effected by agarose, agarose-acrylamide or polyacrylamide gel electrophoresis using standard methodology (see, e.g., Sambrook, et al., Molecular Cloning, Fritsch and Maniatis, eds., Cold Spring Harbor Lab. Press, Cold Spring Harbor, N.Y. (1989)). Alternatively, chromatography can be used to effect separation. Examples of chromatography include adsorption, partition, ion-exchange and molecular sieve, and examples of types of chromatographic techniques include column, paper, thin-layer and gas chromatography (see, e.g., Freifelder, Physical Biochemistry Applications to Biochemistry and Molecular Biology, 2nd ed., Wm. Freeman & Co., New York, N.Y. (1982)).

k. Detection

The method of identifying also includes detecting the one or more SNPs in KRAS. This detecting step includes detecting or measuring the first amplicon and/or the second amplicon, and the third amplicon.

As described above, each probe in the reaction mixture may contain a different label and thus, can be distinctly detected. In some embodiments, probes that detect that same amino acid substitution, but a different nucleotide change in the respective codon, may contain the same label. This distinct detection, in turn, provides for the identification of the absence or presence of the one or more SNPs in the KRAS gene. Detection may be simultaneous with amplification. Accordingly, in a single reaction mixture, 1, 2, 3, 4, 5, 6, 7, 8, 9, 10, 11, 12, 13, 14, 15, 16, 17, 18, 19, 20, or more different probes may be used, each probe containing a different label, thereby allowing for distinct detection of each probe. In turn, this distinct detection provides for the identification of the absence or presence of 1, 2, 3, 4, 5, 6, 7, 8, 9, 10, 11, 12, 13, 14, 15, 16, 17, 18, 19, 20, or more SNPs in the KRAS gene in the single reaction mixture.

In some embodiments, amplification and detection can be combined in a real-time PCR assay. When real-time PCR is used, the detectably labeled probe permits detection only after the probe selectively hybridizes with its complementary nucleic acid sequence, thereby enabling simultaneous amplification and detection. When a detectably labeled probe is present in the reaction mixture during amplification, the detectably labeled probe should be stable under the conditions that promote amplification, should not interfere with amplification, should bind to its target sequence under amplification conditions, and emit a signal only upon binding its target sequence. Examples of detectably labeled probes that are particularly well-suited in this regard include molecular beacon detectable oligonucleotides, TAQMAN® detectable oligonucleotides, and linear detectable oligonucleotides, such as those described by Abravaya, et al. (U.S. Pat. App. Pub. No. 2005/0227257). The detectably labeled probes can form the loop region, alone or in further combination with part of the stem region, of a molecular beacon. The detectably labeled probes also can be used as linear detectable oligonucleotides with a fluorophore (e.g., FAM) at one end and a high-efficiency quencher, such as the Black Hole Quencher (BHQ®; BioSearch Technologies, Inc., Novato, Calif.), at the other end.

If desired, the sample suspected of containing the KRAS target sequence or the detectably labeled probe may be immobilized on a solid support to facilitate detection. Examples of assay formats utilizing solid supports include dot-blot formats and reverse dot-blot formats (see, e.g., U.S. Pat. Nos. 5,310,893; 5,451,512; 5,468,613; and 5,604,099, all of which are specifically incorporated herein by reference for their teachings regarding same).

In other embodiments, amplification may be detected by visualization. For example, a gel stained with ethidium bromide can be visualized with UV light. Amplification products labeled with a radioisotope can be visualized by exposing and developing an x-ray film, whereas amplification products labeled with a fluorometric label can be visualized by subjecting the amplification products to stimulating spectra. A preferred method of visualization of amplification is the use of a labeled detectable oligonucleotide that hybridizes to the amplified products. A manual column, such as one available from Qiagen, also can be used.

In still other embodiments, dideoxy sequencing-based methods and Pyrosequencing™ of oligonucleotide-length products also can be used to detect amplified nucleic acid. Another sequencing method is described by Kobayashi, et al., Mol. Cell. Detectable oligonucleotides 9: 175-182 (1995)).

l. Determination of ΔCN

The method of identifying also includes determining the difference in cycle number (ΔCN) for each reaction mixture. The ΔCN is the difference between the cycle number (CN) for amplification of the KRAS mutant sequence and the CN for amplification of the internal control. The ΔCN value for each SNP is evaluated against a fixed cutoff value, in which if the ΔCN is less than the fixed cutoff value, then the respective SNP is detected. Each fixed cutoff value is unique to the combination of the SNP being detected and the label contained on the respective probe. Accordingly, the smaller the ΔCN for a given SNP, an increased likelihood (i.e., higher percentage) exists that the SNP is present in the KRAS target sequence.

In some embodiments, if more than one SNP is detected, the SNP with the smallest relative ΔCN is reported as being detected because mutations in the KRAS gene are "driver" mutations. Such driver mutations drive oncogenesis and thus, no selective advantage exists within a primary tumor for more than one mutation. Accordingly, if a primary tumor contains a mutation in the KRAS gene, one mutation or SNP is often expected.

The method of identifying, however, should not be considered limited to detecting only one SNP in the KRAS gene. In some embodiments, it may be desirable to report all SNPs having a respective ΔCN less than the corresponding fixed cutoff value as being detected. Reporting may include a rank order of the detected SNPs with the SNP with the smallest relative ΔCN being ranked first and the SNP with the largest relative ΔCN being ranked last, thereby providing a user of the method of identifying with an ordered list of the detected SNPs in the KRAS gene.

In some embodiments, no SNP may be detected in the reaction mixture, i.e., the ΔCN for any given SNP is not less than the respective fixed cutoff value. This is determined to be a true or accurate negative result when amplification of the internal control (i.e., detection of the third amplicon) indicates that sufficient KRAS target sequence was present in the reaction mixture to detect low-percentage SNPs. On the other hand, if amplification of the internal control (i.e., detection of the third amplicon) indicates that insufficient KRAS target sequence was present in the reaction mixture to detect low-percentage SNPs, then the negative result may be a false negative result, thereby indicating that the user of the method of identifying should repeat the method with a sample expected to provide a larger amplifiable amount of the KRAS target sequence. Accordingly, amplification of the internal control (i.e., generation and detection of the third amplicon) determines the quantity of amplifiable KRAS target sequence present in the reaction mixture, and thus, indicates if the reaction mixture and amplification conditions were sufficiently sensitive to permit accurate reporting of no SNP being detected in the KRAS gene.

3. METHOD OF SELECTING A CANCER THERAPY

Provided herein is a method for selecting a cancer therapy or treatment for the subject in need thereof. The method may apply the method of identifying the presence or absence of the one or more SNPs in KRAS described above to select a treatment for the subject. Upon selection, the method may also include administering the treatment to the subject.

If the one or more SNPs in KRAS are detected, then a user of the method of selecting, in some embodiments, may select a therapy that does not target epidermal growth factor receptor (EGFR). Selecting may include administering to the subject a therapy other than a therapy targeting epidermal growth factor receptor (EGFR) when the one or more SNPs are identified as being present in KRAS.

As described above, EGFR acts upstream of KRAS in the MAPK signaling pathway and the one or more SNPs in the KRAS gene render KRAS constitutively active. Accordingly, in CRC and NSCLC, therapies targeting EGFR may be less effective if the one or more SNPs are present in the KRAS gene because the downstream part of the MAPK pathway is not inhibited by the EGFR therapy given the constitutive activity of the mutant KRAS. In some embodiments, the method of selecting may include not administering a therapy targeting EGFR to the subject when the method described herein detects the one or more SNPs in KRAS.

If the one or more SNPs in KRAS are not detected, then the user of the method of selecting, in some embodiments, may select a therapy targeting EGFR as a cancer therapy for the subject. Accordingly, in some embodiments, the method of selecting may include administering a therapy targeting EGFR to the subject when the method described herein does not detect the one or more SNPs in KRAS.

4. METHOD OF PREDICTING A RESPONSE TO A CANCER THERAPY

Also provided herein is a method for predicting a response to a cancer therapy or treatment in a subject in need thereof. The method may apply the method of identifying the presence or absence of one or more SNPs in KRAS described above to predict the response of the subject to a given cancer therapy.

In some embodiments, if the one or more SNPs were identified as being present in the KRAS gene of the subject, this would allow the user of the method to predict that the subject may have a decreased likelihood of responding to a therapy targeting EGFR. Accordingly, the subject containing the one or more SNPs may be administered a therapy that does not target EGFR.

In other embodiments, if the one or more SNPs were not identified as being present in the KRAS gene of the subject, this would allow the user of the method to predict that the subject may have an increased likelihood of responding to the therapy targeting EGFR. Accordingly, the subject not containing the one or more SNPs may be administered the therapy targeting EGFR.

5. KIT

Also provided herein is a kit for use with the methods disclosed herein. The kit may include the primers, probes, PNA oligomer, and internal control described herein, each of which may be contained within a single container or combined in any combination in one or more containers. The kit may also include the positive and negative controls described above. The kit may further include the nucleic acid amplification reagents described above. The kit may also include other material(s), which may be desirable from a user standpoint, such as a buffer(s), a diluent(s), a standard(s), and/or other material useful in sample processing, washing, or conducting any other step of the method described herein.

The kit according to the present disclosure preferably includes instructions for carrying out the method of the invention. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site which provides instructions.

The present invention has multiple aspects, illustrated by the following non-limiting examples.

6. EXAMPLES

Example 1

Materials and Methods for Examples 2-8

Specimen Collection.

Fixed-formalin paraffin-embedded (FFPE) sections (5 to 10 micron) were prepared from human NSCLC tissue, CRC tissue, or the cell lines specified below. For FFPE sections mounted on slides, the section was scraped off the slide (e.g., using a scalpel or single-edge razor blade) and transferred to a labeled tube for DNA extraction as described below. For FFPE sections not mounted on slides, the sections was transferred to a labeled tube for DNA extraction as described below. The total tissue area in each tube was at least 4 mm$^2$.

Instrumentation.

The m2000rt instrument from Abbott Laboratories was used for the real-time PCR.

Genomic DNA Extraction from FFPE Samples.

Genomic DNA was extracted from FFPE samples using the TargetPrep DNA FFPE Sample Preparation Kit I and II (Abbott Laboratories), following the manufacturer's instructions. Briefly, FFPE samples were deparaffinized using xylene or Hemo-De and then incubated in Lysis Solution 1 with proteinase K to release DNA. An incubation step at an elevated temperature partially reversed formalin cross-linking of the released nucleic acids, improving DNA yield and quality. The lysate was then mixed with Lysis Buffer 2 and ethanol to provide appropriate binding conditions for DNA, followed by application of the sample to a DNA Elution Spin Column where DNA bound to a silica membrane. The bound DNA was washed with Wash Buffer 1 and then Wash Buffer 2 to remove impurities. The bound DNA was eluted with Elution buffer and then used for PCR amplification.

Amplification and Detection.

Amplification reagents were combined into 3 unique master mixes. The purified DNA sample was combined with each master mix in a 96-well optical reaction plate (i.e., 3 PCR wells for each sample). After sealing the plate with optical film, the plate was then transferred to the m2000rt instrument for amplification and detection of KRAS mutations. Further details on the amplification and detection are provided below.

The first master mix contained the reagents shown in Table 9 below. Table 9 also shows the final reaction concentration of each reagent.

TABLE 9

| Reagent | Final Reaction Concentration |
| --- | --- |
| G12S probe (SEQ ID NO: 22) | 0.20 µM |
| G12C probe (SEQ ID NO: 27) | 0.20 µM |
| G12R probe (SEQ ID NO: 30) | 0.20 µM |
| Exon 2 forward primer (SEQ ID NO: 2) | 0.50 µM |
| Exon 2 reverse primer (SEQ ID NO: 6) | 0.50 µM |
| Exon 2 PNA oligomer (SEQ ID NO: 52) | 0.80 µM |
| IC forward primer (SEQ ID NO: 43) | 0.25 µM |
| IC reverse primer (SEQ ID NO: 48) | 0.25 µM |
| IC probe (SEQ ID NO: 51) | 0.10 µM |
| Buffer* | 1X |
| ROX reference | 0.06 µM |
| dNTPs | 0.80 mM |
| Activation reagent (MgCl$_2$)** | 7 mM |
| Thermostable Taq DNA polymerase | 11 units/reaction |

*The buffer was suitable for a PCR assay utilizing primers, probes, and an internal control.
**The activation reagent was in buffer containing MgCl$_2$ and Tris. MgCl$_2$ was a co-factor of the DNA polymerase.

The second master mix contained the reagents shown in Table 10 below. Table 10 also shows the final reaction concentration of each reagent.

TABLE 10

| Reagent | Final Reaction Concentration |
| --- | --- |
| G12D probe (SEQ ID NO: 13) | 0.20 µM |
| G12A probe (SEQ ID NO: 16) | 0.20 µM |
| G12V probe (SEQ ID NO: 20) | 0.20 µM |
| Exon 2 forward primer (SEQ ID NO: 2) | 0.50 µM |
| Exon 2 reverse primer (SEQ ID NO: 6) | 0.50 µM |
| Exon 2 PNA oligomer (SEQ ID NO: 52) | 0.80 µM |
| IC forward primer (SEQ ID NO: 43) | 0.25 µM |
| IC reverse primer (SEQ ID NO: 48) | 0.25 µM |
| IC probe (SEQ ID NO: 51) | 0.10 µM |
| Buffer* | 1X |

TABLE 10-continued

| Reagent | Final Reaction Concentration |
|---|---|
| ROX reference | 0.06 μM |
| dNTPs | 0.80 mM |
| Activation reagent (MgCl$_2$)** | 7 mM |
| Thermostable Taq DNA polymerase | 11 units/reaction |

*The buffer was suitable for a PCR assay utilizing primers, probes, and an internal control.

**The activation reagent was in buffer containing MgCl$_2$ and Tris. MgCl$_2$ was a co-factor of the DNA polymerase.

The third master mix contained the reagents shown in Table 11 below. Table 11 also shows the final reaction concentration of each reagent.

TABLE 11

| Reagent | Final Reaction Concentration |
|---|---|
| G13D probe (SEQ ID NO: 31) | 0.20 μM |
| Q61Ha probe (SEQ ID NO: 38) | 0.20 μM |
| Q61Hb probe (SEQ ID NO: 40) | 0.20 μM |
| G13C probe (SEQ ID NO: 34) | 0.20 μM |
| Exon 3 forward primer (SEQ ID NO: 7) | 0.50 μM |
| Exon 3 reverse primer (SEQ ID NO: 11) | 0.50 μM |
| Exon 3 PNA oligomer (SEQ ID NO: 56) | 1.20 μM |
| Exon 2 forward primer (SEQ ID NO: 2) | 0.50 μM |
| Exon 2 reverse primer (SEQ ID NO: 6) | 0.50 μM |
| Exon 2 PNA oligomer (SEQ ID NO: 52) | 0.80 μM |
| IC forward primer (SEQ ID NO: 43) | 0.25 μM |
| IC reverse primer (SEQ ID NO: 48) | 0.25 μM |
| IC probe (SEQ ID NO: 51) | 0.10 μM |
| Buffer* | 1X |
| ROX reference | 0.06 μM |
| dNTPs | 0.80 mM |
| Activation reagent (MgCl$_2$)** | 7 mM |
| Thermostable Taq DNA polymerase | 11 units/reaction |

*The buffer was suitable for a PCR assay utilizing primers, probes, and an internal control.

**The activation reagent was in buffer containing MgCl$_2$ and Tris. MgCl$_2$ was a co-factor of the DNA polymerase.

Additionally, positive and negative control reagents were included within each run and were processed through the DNA extraction, amplification, and detection steps of the method to assess run validity. Specifically, the negative control reagent included a plasmid encoding the internal control at a level of 6.67×10$^5$ copies/mL and TE buffer with carrier DNA. The internal control was a region of the KRAS gene that has no known incidence of mutation. The positive control reagent included a plasmid encoding the internal control (present at a level of 6.67×10$^5$ copies/mL), two plasmids encoding targeted SNPs (each at 1.00×10$^5$ copies/mL, in which one plasmid encoded G12R and G12D and the other plasmid encoded G13D and Q61Ha), and TE buffer with carrier DNA. Accordingly, the positive control reagent generated an amplicon for every primer pair per reaction and at least one positive signal in each fluorescence channel being used to monitor amplification in the method. The positive and negative control reagents were used to monitor sample preparation, amplification, and detection as well as for contamination.

Cycling conditions on the m2000rt instrument were as shown in Table 12 below. Ramping was fast, volume setting was 50 μl, and reaction volume was 80 μl.

TABLE 12

| Step Number | Number of Cycles | Temperature | Time |
|---|---|---|---|
| 1 | 1 | 93.5° C. | 10 minutes |
| 2 | 1 | 73.5° C. | 10 minutes |
| 3 | 3 | 92° C. | 15 seconds |
|   |   | 73.5° C. | 30 seconds |
|   |   | 61° C. | 60 seconds |
| 4 | 45 | 92° C. | 15 seconds |
|   |   | *61° C. | 90 seconds |

*Real time fluorescence measurements were conducted at each cycle during this step.

Each probe contained a 5' fluorescent label and a 3' quencher moiety as shown below in Table 13, thereby allowing for the independent detection of each probe in its respective well of the optical reaction plate. This independent detection, in turn, provided the ability to detect and identify each SNP when present in the KRAS gene.

Specifically, within any given well of the optical reaction plate, each probe contained a different fluorophore and was detected by a unique fluorescence channel on the m2000rt instrument. This setup allowed for the simultaneous amplification and detection of the internal control and any of three mutations (i.e., SNPs), if present, in a single well of the optical reader plate. Accordingly, the 3-reactions per patient setup allowed for the detection of nine independent SNPs in the KRAS gene.

TABLE 13

| Probe | 5' Fluorescent Label | 3' Quencher Moiety |
|---|---|---|
| G12D probe (SEQ ID NO: 13) | FAM | BHQ1 |
| G12A probe (SEQ ID NO: 16) | VIC | BHQ1 |
| G12V probe (SEQ ID NO: 20) | Quasar | BHQ2 |
| G12S probe (SEQ ID NO: 22) | Quasar | BHQ2 |
| G12C probe (SEQ ID NO: 27) | FAM | BHQ1 |
| G12R probe (SEQ ID NO: 30) | VIC | BHQ1 |
| G13D probe (SEQ ID NO: 31) | FAM | BHQ1 |
| G13C probe (SEQ ID NO: 34) | VIC | BHQ1 |
| Q61Ha probe (SEQ ID NO: 38) | Quasar | BHQ2 |
| Q61Hb probe (SEQ ID NO: 40) | Q670 | BHQ2 |
| IC probe (SEQ ID NO: 51) | NED | BHQ2 |

Example 2

Mutation Inclusivity

The capability of the method described above to distinguish G12D, G12A, G12V, G12S, G12C, G12R, G13D, and G13C from each other and from G12, G13, G13A, G13V, G13S, and G13R, as well as Q61H from Q61, Q61P, Q61E, Q61K, Q61L, and Q61R, was evaluated. KRAS wild-type human cell line DNA or KRAS wild-type human cell line DNA spiked with a plasmid containing the listed mutation at a frequency of one copy per haploid genome were tested in replicates of three. The presence or absence of each mutation was accurately determined in each case as shown in Table 14 below. Accordingly, the method described above accurately identified each targeted SNP and did not detect SNPs or wild-type sequences that were not targeted for detection.

TABLE 14

| Assay Target | KRAS Mutation[a,b] | Reported Result | Interpretation |
|---|---|---|---|
| Targeted | G12D (G_AT) | G12D | Mutation Detected |
|  | G12A (G_CT) | G12A | Mutation Detected |
|  | G12V (G_TT) | G12V | Mutation Detected |
|  | G12S (_AGT) | G12S | Mutation Detected |
|  | G12C (_TGT) | G12C | Mutation Detected |
|  | G12R (_CGT) | G12C | Mutation Detected |
|  | G13D (GA_C) | G13D | Mutation Detected |
|  | G13C (_TGC) | G13C | Mutation Detected |
|  | Q61Ha (CA_C) | Q61H | Mutation Detected |
|  | Q61Hb (CA_T) | Q61H | Mutation Detected |
| Not Targeted | G12 (GGT) | Not Detected | Not Detected |
|  | G13 (GGC) | Not Detected | Not Detected |
|  | Q61 (CAA) | Not Detected | Not Detected |
|  | Q61 (CAG) | Not Detected | Not Detected |
|  | G13A (G_CC) | Not Detected | Not Detected |
|  | G13V (G_TC) | Not Detected | Not Detected |
|  | G13S (_AGC) | Not Detected | Not Detected |
|  | G13R (_CGC) | Not Detected | Not Detected |
|  | Q61P (C_CA) | Not Detected | Not Detected |
|  | Q61E (_GAA) | Not Detected | Not Detected |
|  | Q61K (_AAA) | Not Detected | Not Detected |
|  | Q61L (_CTA) | Not Detected | Not Detected |
|  | Q61R (CG_A) | Not Detected | Not Detected |

[a]KRAS mutation (codon with mutant nucleotide underlined).
[b]G12, G13, and Q61 represented wild-type.

Example 3

FFPE (Fixed-Formalin Paraffin-Embedded) Section Type

The method described above was further evaluated for use with FFPE sections mounted and not mounted on slides. Specifically, the agreement between the section types (1) FFPE section mounted on slides and (2) FFPE section not mounted on slides was evaluated with a total of 50 FFPE samples (i.e., 22 CRC specimens, 24 NSCLC specimens, and 4 cell line samples). Each FFPE cell line sample consisted of a mixture of a cell line containing a specific KRAS mutation (G12R, G12D, G13C, or Q61H) and a KRAS wild-type cell line. The cell line samples were mixed to generate a 5% mutant cell line frequency and subsequently fixed in formalin and embedded in paraffin. As shown in Table 15, 30 of the 50 samples had an interpretation of "Mutation Detected" for both section types. 20 of the 50 samples had an interpretation of "Not Detected" for both section types. These results demonstrated 100% (50/50) overall agreement between section types (i.e., FFPE section mounted on slides and FFPE section not mounted on slides). Accordingly, these data also demonstrated that the method described above did not discriminate between FFPE sections that were and were not mounted on slides.

TABLE 15

|  |  | FFPE Sections Not Mounted on Slides | |
|---|---|---|---|
|  |  | Mutation Detected | Not Detected |
| FFPE Sections Mounted on Slides | Mutation Detected | 30 | 0 |
|  | Not Detected | 0 | 20 |

Example 4

Analytical Sensitivity

The method described above was also evaluated for analytical sensitivity. Specifically, DNA from KRAS mutant and wild-type FFPE cells lines was extracted and purified. Each KRAS mutant DNA purification was blended with KRAS wild-type DNA purification to achieve a mutation frequency of either 4.0% in 10 ng of amplifiable genomic DNA or 8.0% in 2 ng of amplifiable genomic DNA. Each 10 ng blend was subsequently diluted to generate a panel with mutation frequencies of 4.0%, 2.0%, 1.0%, 0.5%, and 0.25%. Each 2 ng blend was subsequently diluted to generate a panel with mutation frequencies of 8.0%, 4.0%, 2.0%, 1.0%, and 0.5%. For each panel, a total of six runs were performed using two lots of amplification reagents and 3 m2000rt instruments. Eight replicates of each panel were included in each run, yielding a total of 48 tests per panel.

The detection percentage for each 10 ng panel and each 2 ng panel are shown below in Tables 16 and 17, respectively. Probit data analysis was used to determine mutation percentage detection with 95% probability at either 10 ng or 2 ng of amplifiable genomic DNA and is shown in Table 18 below. These data demonstrated that the analytical sensitivity for the method was 2% KRAS mutation in 10 ng of amplifiable genomic DNA.

TABLE 16

| Mutation | Mutation Percentage (%) | | | | |
|---|---|---|---|---|---|
|  | 4.0 | 2.0 | 1.0 | 0.5 | 0.25 |
| G12C | 98 | 100 | 85 | 40 | 13 |
| G12S | 100 | 100 | 94 | 44 | 17 |
| G12R | 100[c] | 100 | 96 | 83 | 52 |
| G12D | 100 | 100 | 100 | 96 | 48 |
| G12V | 100 | 100 | 98 | 79 | 38 |
| G12A | 100 | 100 | 100 | 98[c] | 65 |
| G13C | 100 | 100 | 100 | 100 | 92 |
| G13D | 100 | 100 | 94 | 56 | 23 |
| Q61H[a] | 100 | 100 | 100 | 100 | 90 |
| Q61H[b] | 100 | 100 | 100 | 60 | 17 |

[a]Q61H codon CAC
[b]Q61H codon CAT
[c]One replicate with an invalid result was excluded from the analysis.

TABLE 17

| Mutation | Mutation Percentage (%) | | | | |
|---|---|---|---|---|---|
| | 8.0 | 4.0 | 2.0 | 1.0 | 0.5 |
| G12C | 98 | 100 | 98 | 71 | 54 |
| G12S | 100 | 100 | 79 | 10 | 2 |
| G12R | 100 | 100 | 100 | 90 | 56 |
| G12D | 100 | 100 | 100 | 58 | 31 |
| G12V | 100 | 100 | 98 | 83 | 60 |
| G12A | 100 | 100 | 100 | 100 | 85 |
| G13C | 100 | 100 | 100 | 92 | 85 |
| G13D | 100 | 98 | 71 | 29 | 6 |
| Q61H[a] | 100 | 100 | 96 | 85 | 63 |
| Q61H[b] | 100 | 98 | 94 | 33 | 10 |

[a]Q61H codon CAC
[b]Q61H codon CAT

TABLE 18

| Mutation | Amplifiable Genomic DNA | |
|---|---|---|
| | 10 ng | 2 ng |
| G12C | 1.7% | 1.9% |
| G12S | 1.2% | 2.8% |
| G12R | 0.9% | 1.2% |
| G12D | 0.5% | 1.9% |
| G12V | 0.8% | 1.6% |
| G12A | 0.4% | 0.5% |
| G13C | 0.3% | 1.0% |
| G13D | 1.1% | 3.7% |
| Q61H[a] | 0.3% | 1.7% |
| Q61H[b] | 0.9% | 2.7% |

[a]Q61H codon CAC
[b]Q61H codon CAT

Example 5

Reproducibility

The reproducibility of the method described above was also evaluated. Reproducibility was demonstrated using an 11-member panel of FFPE homogenate of CRC and NSCLC specimens. The results of this study are shown below in Table 19 below.

Panel members 01 to 09 represented targeted KRAS mutations. Panel members 10 and 11 represented KRAS wild-type. This study also included 4 low-positive samples (i.e., panel members 01, 05, 08, and 09) that were targeted to a genomic DNA input of less than or equal to 10 ng and mutation percentage of less than or equal to 5%. The study was completed using three amplification reagent lots/instruments/operators with two sample preparations per panel member and 2 m2000rt instrument runs per day for six days.

The method had an overall agreement of 100% (791/791) for all panel members, replicates, operators, reagent lots, instruments, and days combined, with an agreement of 100% (144/144) for "Not Detected" panel members and an agreement of 100% (647/647) for "Mutation Detected" panel members. Accordingly, these data demonstrated that the method described above produced reproducible results, namely at a rate of 100% reproducibility.

TABLE 19

| Panel Member | Expected Result | FFPE Tumor Type | Valid Results | Mutation Detected | Not Detected | % Agreement[a] | Lower Bound One-sided 95% Coincidence |
|---|---|---|---|---|---|---|---|
| 01 | Mutation Detected (G12C) | NSCLC | 72 | 72 | 0 | 100 | 95.9 |
| 02 | Mutation Detected (G12S) | CRC | 72 | 72 | 0 | 100 | 95.9 |
| 03 | Mutation Detected (G12R) | NSCLC | 71[b] | 71 | 0 | 100 | 95.9 |
| 04 | Mutation Detected (G12D) | CRC | 72 | 72 | 0 | 100 | 95.9 |
| 05 | Mutation Detected (G12V) | CRC | 72 | 72 | 0 | 100 | 95.9 |
| 06 | Mutation Detected (G12A) | CRC | 72 | 72 | 0 | 100 | 95.9 |
| 07 | Mutation Detected (G13D) | CRC | 72 | 72 | 0 | 100 | 95.9 |
| 08 | Mutation Detected (Q61H) | NSCLC | 72 | 72 | 0 | 100 | 95.9 |
| 09 | Mutation Detected (G13C) | NSCLC | 72 | 72 | 0 | 100 | 95.9 |
| 10 | Not Detected | NSCLC | 72 | 0 | 72 | 100 | 95.9 |
| 11 | Not Detected | CRC | 72 | 0 | 72 | 100 | 95.9 |

[a]Replicates from panel members 01 to 09 that had a valid result listing the expected KRAS mutation and an interpretation of "Mutation Detected" were considered in agreement. Replicates from panel members 10 and 11 that had a valid result and an interpretation of "Not Detected" were considered in agreement.
[b]One replicate with an invalid result was excluded from analysis.

Example 6

Correlation to Reference Method

The method described above was compared to another method of detecting SNPs, namely 2× Bi-directional Sanger sequencing. Eighty-one NSCLC and 97 CRC FFPE specimens were processed using TargetPrep DNA FFPE Sample Preparation Kits I and II. The same DNA-containing eluate was tested by the method described above and 2× Bi-directional Sanger sequencing. Mutation detection was considered to be in positive agreement if the identical mutation was detected by both methods. The agreements are shown below in Tables 20, 21, and 22 for NSCLC, CRC, and combined NSCLC and CRC, respectively.

The overall agreement between the method described above and 2× Bi-directional Sanger sequencing for NSCLC specimens was 95.1% (77/81) with a positive agreement of 92.9% (13/14). Of the 13 mutations found to be in positive agreement, the following mutations were observed (instances): G12C (6), G12D (1), G12V (2), G13D (1), G13C (1), and Q61H (2).

The overall agreement between the method described above and 2× Bi-directional Sanger sequencing for CRC specimens was 86.6% (84/97) with a positive agreement of 97.6% (41/42). Of the 41 mutations found to be in positive agreement, the following mutations were observed (instances): G12S (1), G12C (1), G12D (12), G12V (9), G13D (15), and Q61H (3).

The overall agreement between the method described above and 2× Bi-directional Sanger sequencing for NSCLC and CRC specimens combined was 90.4% (161/178) with a positive agreement of 96.4% (54/56). Of the 54 mutations found to be in positive agreement, the following mutations were observed (instances): G12S (1), G12C (7), G12D (13), G12V (11), G13D (16), G13C (1), and Q61H (5).

In summary, these data demonstrated 86% or higher overall agreement and 92% or higher positive agreement between the method described above and 2× Bi-directional Sanger sequencing.

TABLE 20

| | | 2X Bi-directional Sanger Sequencing | |
| --- | --- | --- | --- |
| | | Mutation Detected | Not Detected |
| Method Described Above | Mutation Detected | 13 | 3[a] |
| | Not Detected | 1[b] | 64 |

[a]Bi-directional Sanger sequencing had a limit of detection of approximately 20% mutation content in FFPE specimens. Presence and identity of each mutation was confirmed by Qiagen therascreen RGQ PCR.
[b]Mutation identified by 2X Bi-directional Sanger sequencing was G13D. Next generation sequencing of the specimen using the Ion AmpliSeq Cancer Hotspot Panel v2 indicated wild-type sequences at codons 12, 13, and 61. Absence of a mutation was also confirmed by Qiagen therascreen RGQ PCR.

TABLE 21

| | | 2X Bi-directional Sanger Sequencing | |
| --- | --- | --- | --- |
| | | Mutation Detected | Not Detected |
| Method Described Above | Mutation Detected | 41 | 12[a] |
| | Not Detected | 1[b] | 43 |

[a]Bi-directional Sanger sequencing had a limit of detection of approximately 20% mutation content in FFPE specimens. Two specimens with Q61H mutations were confirmed by next generation sequencing using the Ion AmpliSeq Cancer Hotspot Panel v2. Ten specimens had a codon 12 or 13 mutation. Presence and identity of 9 mutations were confirmed by Qiagen therascreen RGQ PCR. Presence of the remaining mutation was confirmed by Qiagen therascreen RGQ PCR; however, mutation identity differed (G12A mutation identified by the method described herein and G12S mutation identified by Qiagen therascreen RGQ PCR).
[b]Mutation identified by 2X Bi-directional Sanger sequencing was G13D. Next generation sequencing of the specimen using Ion AmpliSeq Cancer Hotspot Panel v2 indicated wild-type sequences at codons 12, 13, and 61. Absence of a mutation was also confirmed by Qiagen therascreen RGQ PCR.

TABLE 22

| | | 2X Bi-directional Sanger Sequencing | |
| --- | --- | --- | --- |
| | | Mutation Detected | Not Detected |
| Method Described Above | Mutation Detected | 54 | 15[a] |
| | Not Detected | 2[b] | 107 |

[a]Bi-directional Sanger sequencing had a limit of detection of approximately 20% mutation content in FFPE specimens. Two specimens with Q61H mutations were confirmed by next generation sequencing using the Ion AmpliSeq Cancer Hotspot Panel v2. Thirteen specimens had a codon 12 or 13 mutation. Presence and identity of the 12 mutations was confirmed by Qiagen therascreen RGQ PCR. Presence of the remaining mutation was confirmed by Qiagen therascreen RGQ PCR; however, mutation identity differed (G12A mutation identified by the method described herein and G12S mutation identified by Qiagen therascreen RGQ PCR).
[b]Mutation identified by 2X Bi-directional Sanger sequencing was G13D for each specimen. Next generation sequencing of each specimen using the Ion AmpliSeq Cancer Hotspot Panel v2 indicated wild-type sequences at codons 12, 13, and 61 in each specimen. Absence of a mutation in each specimen was also confirmed by Qiagen therascreen RGQ PCR.

Example 7

Analytical Specificity

The method described above was also evaluated for its analytical specificity. Analytical specificity was evaluated using human placental derived DNA, which contained KRAS homologs hRAS and nRAS and the KRAS pseudogene KRAS1P. The human placental derived DNA was tested in replicates of three at genomic DNA input of 25 ng and no cross-reactivity was observed.

In addition, four lung-related microorganisms and three colon-related microorganisms were evaluated for potential cross-reactivity in the method described above (see Table 23 below). Each microorganism was added at $10^6$ colony-forming units (CFUs) or $10^6$ genomic copies to samples negative for KRAS mutations during the lysis step of sample processing and tested in replicates of three. No cross-reactivity was observed with any of the microorganisms tested.

Additionally, KRAS mutation-positive samples were evaluated for interference by the microorganisms. KRAS mutant plasmids were added to 10 ng of KRAS wild-type human cell line DNA at a 2% copy frequency and tested in replicates of three by the method in the presence of each of the microorganisms at $10^6$ CFUs or $10^6$ genomic copies per sample input. None of the microorganisms interfered with KRAS mutation detection.

In summary, these data demonstrated that the method described above did not cross-react with KRAS homologs or pseudogene, and thus, the method was specific for KRAS. The specificity of this method was further demonstrated by the lack of cross-reactivity with and interference by microorganisms that may contaminate a sample obtained from a subject.

TABLE 23

| Microorganism | Related Organ | Sample Type | Targeted Concentration per Sample Output |
| --- | --- | --- | --- |
| Bacteroides caccae | Colon | Cultured microorganisms | $10^6$ CPU |
| Prevotella intermedia | Colon | Purified nucleic acids | $10^6$ genome copies |
| Escherichia coli | Colon | Purified nucleic acids | $10^6$ genome copies |
| Staphylococcus aureus | Lung | Purified nucleic acids | $10^6$ genome copies |
| Pseudomonas aeruginosa | Lung | Purified nucleic acids | $10^6$ genome copies |
| Klebsiella pneumonia | Lung | Purified nucleic acids | $10^6$ genome copies |
| Aspergillus fumigatus | Lung | Purified nucleic acids | $10^6$ genome copies |

Example 8

Potentially Interfering Substances

The susceptibility of the method described above to interference by elevated levels of substances potentially present in clinical specimens was also evaluated. Samples negative for KRAS mutations (i.e., KRAS wild-type FFPE human cell line) and samples positive for KRAS mutations (i.e., KRAS wild-type FFPE human cell line mixed with KRAS mutant FFPE human cell line resulting in 2% mutation content) were tested with hemoglobin, triglycerides, and necrotic tissue added at the lysis step of sample processing.

For both mutation negative and mutation positive samples, no interference in the reported interpretation and mutation detection results was observed in the presence of up to 4 g/L hemoglobin (2× the Clinical and Laboratory Standards Institute (CLSI) recommended concentration), up to 74 mM triglycerides (2× the CLSI recommended high concentration), and in the presence of an additional 10 micron section of human CRC FFPE tissue with 70% necrotic area. Accordingly, these results demonstrated that the method described above is not interfered with by the presence of (and high levels of) hemoglobin, triglycerides, and necrotic tissue.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

---

What is claimed is:

1. A primer and probe set consisting of:
   (a) a forward primer nucleic acid sequence of SEQ ID NO:2;
   (b) one or more reverse primer nucleic acid sequences selected from: SEQ ID NO:4 and SEQ ID NO:6;
   (c) one or more probe nucleic acid sequences selected from: SEQ ID NO:22, SEQ ID NO:27, and SEQ ID NO:30, wherein each of the one or more probes comprises a fluorescent label and a quencher moiety attached thereto;
   (d) a peptide nucleic oligomer sequence of SEQ ID NO:52;
   (e) an internal control forward primer nucleic acid sequence of SEQ ID NO:43;
   (f) an internal control reverse primer nucleic acid sequence of SEQ ID NO:48; and
   (g) one or more internal control probes comprising the nucleic acid sequence of SEQ ID NO:49, SEQ ID NO:50, and/or SEQ ID NO:51 and a fluorescent label attached thereto,
   wherein each of (a)-(g) are present in a single reaction mixture.

2. A method of identifying the presence or absence of one or more single nucleotide polymorphisms (SNPs) in v-Ki-ras2 Kirsten rat sarcoma viral oncogene homolog (KRAS), the method comprising:
   (a) forming a reaction mixture comprising:
      (i) a sample obtained from a subject, wherein the sample is suspected of containing a KRAS target sequence and
      (ii) the primer and probe set of claim 1;
   (b) subjecting the reaction mixture to conditions sufficient for formation of one or more amplicons; and
   (c) detecting the one or more amplicons.

* * * * *

SEQUENCE LISTING

```
<160> NUMBER OF SEQ ID NOS: 57

<210> SEQ ID NO 1
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 1
tgtgacatgt tctaatatag tcacatt                                            27

<210> SEQ ID NO 2
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 2
gtgtgacatg ttctaatata gtcacatt                                           28

<210> SEQ ID NO 3
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 3
gtgtgacatg ttctaatata gtcaca                                             26

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
gtatcgtcaa ggcactcttg c                                                  21

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 5
gttctcacgg aactgctatg t                                                  21
```

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 6
gtatcgtcaa ggcactcgtg c                                              21

<210> SEQ ID NO 7
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 7
cagactgtgt ttctcccttc tcagg                                          25

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 8
cagactgtgt ttctcccttc tca                                            23

<210> SEQ ID NO 9
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 9
cagactgtgt ttctcccttc tcag                                           24

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
ctggtccctc attgcactgt                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
ctggtccctc attgcactgt                                                20

<210> SEQ ID NO 12
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 12
tactggtccc tcattgcact                                               20

<210> SEQ ID NO 13
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 13
tacgccatca gctc                                                     14

<210> SEQ ID NO 14
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 14
ctacgccatc agct                                                     14

<210> SEQ ID NO 15
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 15
ctacgccatc agctc                                                    15

<210> SEQ ID NO 16
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 16
ccagcagctc caa                                                      13

<210> SEQ ID NO 17
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 17
cgccagcagc tcc                                                      13

<210> SEQ ID NO 18
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 18
tacgccagca gct                                                      13

```
<210> SEQ ID NO 19
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 19
tacgccaaca gctc                                                         14

<210> SEQ ID NO 20
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 20
ctacgccaac agct                                                         14

<210> SEQ ID NO 21
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 21
ctacgccaac agctc                                                        15

<210> SEQ ID NO 22
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 22
tacgccacta gctc                                                         14

<210> SEQ ID NO 23
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 23
ctacgccact agct                                                         14

<210> SEQ ID NO 24
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 24
ctacgccact agctc                                                        15

<210> SEQ ID NO 25
<211> LENGTH: 14
<212> TYPE: DNA
<213> ORGANISM: Artificial Sequence
<220> FEATURE:
<223> OTHER INFORMATION: Synthetic Oligonucleotide
```

```
<400> SEQUENCE: 25
ctacgccaca agct                                                        14

<210> SEQ ID NO 26
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 26
ctacgccaca agctc                                                       15

<210> SEQ ID NO 27
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 27
tacgccacaa gctc                                                        14

<210> SEQ ID NO 28
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 28
ctacgccacg agct                                                        14

<210> SEQ ID NO 29
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 29
ctacgccacg agctc                                                       15

<210> SEQ ID NO 30
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 30
tacgccacga gctc                                                        14

<210> SEQ ID NO 31
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 31
tacgtcacca gctc                                                        14

<210> SEQ ID NO 32
<211> LENGTH: 14
```

```
<212> TYPE: DNA
<213> ORGANISM: Artificial Sequence
<220> FEATURE:
<223> OTHER INFORMATION: Synthetic Oligonucleotide

<400> SEQUENCE: 32
acgtcaccag ctcc                                                       14

<210> SEQ ID NO 33
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 33
acgtcaccag ctcc                                                       14

<210> SEQ ID NO 34
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 34
cgcaaccagc tcca                                                       14

<210> SEQ ID NO 35
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 35
acgcaaccag ctcca                                                      15

<210> SEQ ID NO 36
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 36
acgcaaccag ctcc                                                       14

<210> SEQ ID NO 37
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 37
tcctcgtgac ctgc                                                       14

<210> SEQ ID NO 38
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 38
```
cctcgtgacc tgct                                                      14

<210> SEQ ID NO 39
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 39
ctcctcgtga cctg                                                      14

<210> SEQ ID NO 40
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 40
ctcatgacct gctg                                                      14

<210> SEQ ID NO 41
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 41
actcctcatg accg                                                      14

<210> SEQ ID NO 42
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 42
tactcctcat gacc                                                      14

<210> SEQ ID NO 43
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 43
attaatgaaa tttgttacct gtacacatga                                     30

<210> SEQ ID NO 44
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 44
taatgaaatt tgttacctgt acacatga                                       28

<210> SEQ ID NO 45
<211> LENGTH: 29
<212> TYPE: DNA
<213> ORGANISM: Artificial Sequence

```
<220> FEATURE:
<223> OTHER INFORMATION: Synthetic Oligonucleotide

<400> SEQUENCE: 45
attaatgaaa tttgttacct gtacacatg                                           29

<210> SEQ ID NO 46
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 46
atgttttcga atttctcgaa ctaatgt                                             27

<210> SEQ ID NO 47
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 47
atgttttcga atttctcgaa ctaatgtat                                           29

<210> SEQ ID NO 48
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 48
atgttttcga atttctcgaa ctaatgta                                            28

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 49
gccatcgtat atattcacat t                                                   21

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 50
ccatcgtata tattcacatt ta                                                  22

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
ccatcgtata tattcacatt                                                     20
```

```
<210> SEQ ID NO 52
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 52
cctacgccac cagctcc                                                    17

<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53
tgcctacgcc accagc                                                     16

<210> SEQ ID NO 54
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 54
gcctacgcca ccagc                                                      15

<210> SEQ ID NO 55
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 55
actcctcttg acctgct                                                    17

<210> SEQ ID NO 56
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 56
ctcctcttga cctgctgtg                                                  19

<210> SEQ ID NO 57
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 57
actcctcttg acctgctg                                                   18
```